United States Patent [19]
Au-Young et al.

[11] Patent Number: 5,863,780
[45] Date of Patent: Jan. 26, 1999

[54] HUMAN PROTEIN KINASES

[75] Inventors: Janice Au-Young, Berkeley; Karl J. Guegler, Menlo Park; Phillip R. Hawkins, Mountain View, all of Calif.

[73] Assignee: Incyte Pharmaceuticals, Inc., Palo Alto, Calif.

[21] Appl. No.: 712,709

[22] Filed: Sep. 12, 1996

[51] Int. Cl.$^6$ .............................. C12N 9/12; C07H 21/04
[52] U.S. Cl. .................... 435/194; 435/325; 435/257.33; 435/320.1; 536/23.1; 536/23.2; 536/23.5
[58] Field of Search ................................. 435/194, 240.2, 435/252.1, 320.1, 325, 252.33; 536/23.2, 23.1, 23.5

[56] References Cited

PUBLICATIONS

Creighton, T. E. "Proteins: Structure and Molecular Properties" Second Edition, W.H. Freeman and Company, New York, pp. 108, 109, 132 and 133, 1993.

Webster et al. "Characterization of sgk, a novel memmber of the serine/threonine protein kinase gene family . . . " Mol. Cell. Biol. 13(4), 20–31–2040, Apr. 1993.

*The Protein Kinase Facts Book*, Hardie, G., et al., pp. 58–63 (cAMP–dependent protein kinase (vertebrates) (1995).

*Harrison's Principles of Internal Medicine*, Isselbacher, K.J., et al., 1:416–431 (1994).

*Harrison's Principles of Internal Medicine*, Isselbacher, K.J., et al., 2:1887 (1994).

O'Brian, C.A., et al., "The Tumor Promoter Receptor Protein Kinase C: A Novel Target for Chemoprevention and Therapy of Human Colon Cancer" *Prog. Clin. Biol. Res.*, 391:117–120 (1995).

O'Brian, C.A., et al., "Biology of the protein kinase C family" *Cancer Metast. Rev.*, 8:199–214 (1989).

Saito, N., et al., "α–, βII– and γ–subspecies of protein kinase C localized in hte monkey hippocampus: pre– and post–synaptic localization of γ–subspecies" *Brain Res.*, 656:245–256 (1994).

Ohkusu, K., et al., "Elucidation of the protein kinase C–dependent apoptosis pathway in distinct subsets of T lymphocytes in MRL–lpr/lpr mice" *Eur. J. Immunol.*, 25:3180–3186 (1995).

Wilson, R., et al., "2.2 Mb of contiguous nucleotide sequence from chromosome III of *C. elegans*"*Nature*, 368:32–38 (1994).

Creasy, C.L., et al., "Cloning and Characterization of a Human Protein Kinase with Homology to Ste20" *J. Biol. Chem.*, 270:21695–21700 (1995).

Marra, M., et al., "The WashU–HHMI Mouse EST Project," Database EMEST, Producer EMBL, 3 Aug. 1996, XP002054151, Accession No. AA013892.

Hillier, L., et al., "The WashU–Merck EST project,"Database EMSET, Producer EMBL, 7 Oct. 1995, XP002054152, Accession NO. H59980.

Marra, M., et al., "The WashU–HHMI Mouse EST Project," Databsae EMEST, Producer EMBL, 3 Aug. 1996, XP002054153, Accession No. AA015061,.

*Primary Examiner*—Robert A. Wax
*Assistant Examiner*—Nashaat T. Nashed
*Attorney, Agent, or Firm*—Lucy J. Billings; Sheela Mohan-Peterson; Incyte Pharmaceuticals, Inc.

[57] ABSTRACT

The present invention provides novel human protein kinases (HPK) and polynucleotides which identify and encode HPK. The invention provides for genetically engineered expression vectors and host cells comprising the nucleic acid sequences encoding HPK. The invention also provides for pharmaceutical compositions comprising HPK or antagonists of HPK, and antibodies which specifically bind HPK. Additionally, the invention provides antisense molecules to HPK for treatment or prevention of diseases associated with abnormal expression of HPK.

12 Claims, 20 Drawing Sheets

```
                     9        18        27        36        45        54
5' NNC ATT CTG GGA CCT GTT CGC AGG ACC GTC CGG TGT TCT GGC CCC CTG ATG TCA 63        72        81        90        99       108
   CCT TCA CGG GCC TGA CTC ACA GTC CTA AAT ATC TGA CAG CGA AGA TCG CTT GTA 117       126       135       144       153       162
   GTT CGT GCC CTC GTG AGG CTG GCA TGC AGG ATG GCA GGA CAG CCC GGC CAC ATG 171       180       189       198       207       216
   CCC CAT GGA GGG AGT TCC AAC AAC CTC TGC CAC ACC CTG GGG CCT GTG CAT CCT 225       234       243       252       261       270
   CCT GAC CCA CAG AGG CAT CCC AAC ACG CTG TCT TTT CGC TGC TCG CTG GCG GAC 279       288       297       306       315       324
   TTC CAG ATC GAA AAG ATA GGC CGA GGA CAG TTC AGC GAG AAG GTG TAC AAG GCC 333       342       351       360       369       378
   ACC TGC CTG CTG GAC AGG AAG ACA GTG GCT CTG AAG RAG AAG GTG CAG ATC TTT GAG 387       396       405       414       423       432
   ATG ATG GAC GCC AAG GCG AAG CAG TGT GTC AAG GAG ATC GGC CTC TTG AAG
    M   M   D   A   K   A   K   Q   C   V   K   E   I   G   L   L   K

FIGURE 1A
```

```
                441     450     459     468     477     486
CAA CTG AAC CAC CCA AAT ATC AAG TAT TTG GAC TCC TTT ATC GAA GAC AAC
 Q   L   N   H   P   N   I   K   Y   L   D   S   F   I   E   D   N 495     504     513     522     531     540
GAA CTG AAC ATT GTG CTG GAA TTG GCT GAC GCA GGG GAC CTC CCG CAG ATG ATC
 E   L   N   I   V   L   E   L   A   D   A   G   D   L   P   Q   M   I 549     558     567     576     585     594
AAG TAC TTT AAG AAG CAG AAG CGG CTC ATC CCG GAG AGG ACA GTA TGG AAG TAC
 K   Y   F   K   K   Q   K   R   L   I   P   E   R   T   V   W   K   Y 603     612     621     630     639     648
TTT GTG CAG CTG TGC AGC GCC GTG GAG CAC ATG TCA CGC CGG GTG ATG CAC
 F   V   Q   L   C   S   A   V   E   H   M   S   R   R   V   M   H 657     666     675     684     693     702
CGA GAC ATC AAG CCT GCC AAC GTG TTC ATC ACA GCC ACG GGC GTC GTG AAG CTC
 R   D   I   K   P   A   N   V   F   I   T   A   T   G   V   V   K   L 711     720     729     738     747     756
GGT GAC CTT GGT CTG GGC CGC TTC AGC TCT GAA ACC ACC GCA GCC CAC TCC
 G   D   L   G   L   G   R   F   S   S   E   T   T   A   A   H   S 765     774     783     792     801     810
CTA GTG GGG ACG CCC TAC TAC ATG TCA CCG GAG AGG ATC CAT GAG AAC GGC TAC
 L   V   G   T   P   Y   Y   M   S   P   E   R   I   H   E   N   G   Y
```

FIGURE 1B

```
         819            828            837            846            855            864
AAC TTC AAG TCC GAC ATC TGG TCC TTG GGC TGT CTG TAC GAG ATG GCA GCC
 N   F   K   S   D   I   W   S   L   G   C   L   Y   E   M   A   A 873            882            891            900            909            918
CTC CAG AGC CCC TTC TAT GGA GAT AAG ATG AAT CTC TTC TCC CTG TGC AAG
 L   Q   S   P   F   Y   G   D   K   M   N   L   F   S   L   C   K 927            936            945            954            963            972
ATC GAG TGT GAC TAC CCC CCA CTC CCC GGG GAG CAC TAC TCC GAG AAG TTA
 I   E   C   D   Y   P   P   L   P   G   E   H   Y   S   E   K   L 981            990            999            1008           1017           1026
CGA GAA CTG GTC AGC ATG TGC ATC TGC CCT GAC CCC CAC CAG AGA CCT GAC ATC
 R   E   L   V   S   M   C   I   C   P   D   P   H   Q   R   P   D   I 1035           1044           1053           1062           1071           1080
GGA TAM GTG CAC CAG GTG GCC AAG CAG ATG CAC ATC TGG ATG TCC AGC AMC TGA
 G   X   V   H   Q   V   A   K   Q   M   H   I   W   M   S   S   X 1089           1098           1107           1116           1125           1134
GCG TGG ATG CAC CGT GCC TTA TCA AAG CCA CCA CTT TGC CTT ACT TGA GTC 1143           1152           1161           1170           1179           1188
GTC TTC TCT TCG AGT GGC CAC CTG GTA GCC TAG AAC AGC TAA GAC CAC ANG NTT
```

FIGURE 1C

```
1197           1206      1215      1224      1233           1242
CAG CAG GTT CCC CAA AAG ACT GCC CAG CCT TAC AGC AGA TGC TAA AGG NAG AGC 1251           1260      1269      1278      1287           1296
AGC TGA GNG AGG GGC NCT NNC CAC ATN TCA CTG ATG GTC AGA TTC CAA ANT CCT 1305           1314      1323      1332      1341
TTC TTT ATA CTG TTG TGG ACA ATC TCA GCT GGG TCA ATA AGG GCA GTT GGT TC 3'
```

FIGURE 1D

```
5' CGT TAG GCC CGG GCG TGG CGG GGC CCC GGC GGG GGT CTC CTG GGC CCC
5'                                                                54

9      18      27      36      45      54

CCC CCA CCC ATG GAG CCC GCC GCC GAG GTC GGT CTC AGA CTG AAC TGG
                                                                108
       63      72      81      90      99     108

GCA CCG AGC GCC CCT GGT GTC CCT CGC AGT GGA CTG ACG CCG CGA GCT
                                                                162
      117     126     135     144     153     162

AGC CGG CTC CGC GCC TCT CCG CGG GAT CCA GAC GNC TCC TGG TGG CGG
                                                                216
      171     180     189     198     207     216

AGG GTC TGA CGC GGC GCC ATG GCT CAC CTC CGG GGA TTT GCC AAC CAG CAC
                              M   A   H   L   R   G   F   A   N   Q   H
                                                                270
      225     234     243     252     261     270

TCT CGA GTG GAC CCT GAG GAG CTC TTC ACC AAG CTC GAC CGC ATT GGC AAG GGC
      S   R   V   D   P   E   E   L   F   T   K   L   D   R   I   G   K   G
                                                                324
      279     288     297     306     315     324

TCG TTT GGG GAG GTC TAC AAG GGC ATC GAT AAC CAC ACA AAG GAG GTG GTG GCC
      S   F   G   E   V   Y   K   G   I   D   N   H   T   K   E   V   V   A
                                                                378
      333     342     351     360     369     378

ATC AAG ATC ATC GAC CTG GAG GAG GCC GAG GAT GAG ATC GAG GAC ATC CAG CAG
      I   K   I   I   D   L   E   E   A   E   D   E   I   E   D   I   Q   Q
                                                                432
      387     396     405     414     423     432
```

FIGURE 2A

```
441         450         459         468         477         486
GAG ATC ACT GTC CTC AGT CAG TGC GAC AGC CCC TAC ATC ACC CGC TAC TTT GGC
 E   I   T   V   L   S   Q   C   D   S   P   Y   I   T   R   Y   F   G 495         504         513         522         531         540
TCC TAC CTA AAG AGC ACC AAG CTA TGG ATC ATG GAG TAC CTG GGC GGC GGC
 S   Y   L   K   S   T   K   L   W   I   I   M   E   Y   L   G   G   G 549         558         567         576         585         594
TCA GCA CTG GAC TTG CTT AAA CCA GGT CCC CTG GAG ACA TAC ATT GCC ACG
 S   A   L   D   L   L   K   P   G   P   L   E   T   Y   I   A   T 603         612         621         630         639         648
ATC CTG CGG GAG ATT CTG AAG GGC CTG GAT TAT CTC CAC TCC GAA CGC AAG ATC
 I   L   R   E   I   L   K   G   L   D   Y   L   H   S   E   R   K   I 657         666         675         684         693         702
CAC CGA GAC ATC AAA GCT GCC AAC GTG CTA CTC TCG GAG CAG ACG CAG GGT GAC GTG TTA
 H   R   D   I   K   A   A   N   V   L   L   S   E   Q   T   Q   G   D   V   L 711         720         729         738         747         756
GCT GGC GGA CTT TGG AGC AGG CAG CTC ACA GAC ACG CAG ATT AAG AGG AAC
 A   G   G   L   W   S   R   Q   L   T   D   T   Q   I   K   R   N 765         774         783         792         801         810
ACA TTC GTG GGC ACC CCC TTC TGG ATG GCA CCT GAG GTC ATC GAG AAG CAG TCG GCC
 T   F   V   G   T   P   F   W   M   A   P   E   V   I   E   K   Q   S   A
```

FIGURE 2B

```
        819             828             837             846             855             864
TAC GAC TTC AAG GCT GAC ATC TGG TCC CTG GGG ATC ACA GCC ATC GAG CTC GCC
 Y   D   F   K   A   D   I   W   S   L   G   I   T   A   I   E   L   A 873             882             891             900             909             918
AAG GGG GAG CCT CCA AAC TCT GAC CTC CAC CCC ATG CGC GTC CTG TTC CTG ATT
 K   G   E   P   P   N   S   D   L   H   P   M   R   V   L   F   L   I 927             936             945             954             963             972
CCC AAG AAC AGC CCA ACA CTG GAG GGC CAG CAC AGC AAG CCC TTC AAG GAG
 P   K   N   S   P   T   L   E   G   Q   H   S   K   P   F   K   E 981             990             999            1008            1017            1026
TTC GTG GAG GCC TGC CTC AAC AAA GAC CCC CGA TTC CGG CCC ACG GCC AAG GAG
 F   V   E   A   C   L   N   K   D   P   R   F   R   P   T   A   K   E 1035            1044            1053            1062            1071            1080
CTC CTG AAG CAC AAG TTC ATC ACA CGC TAC ACC AAG AAG ACC TCC TTC CTC ACG
 L   L   K   H   K   F   I   T   R   Y   T   K   K   T   S   F   L   T 1089            1098            1107            1116            1125            1134
GAG CTC ATC GAC CGC TAT AAG CGC TGG AAG TCA GAG GGG CAT GGC GAG GAG TCC
 E   L   I   D   R   Y   K   R   W   K   S   E   G   H   G   E   E   S 1143            1152            1161            1170            1179            1188
AGC TCT GAG GAC TCT GAC ATT GAT GGC GAG GCG GAG GAC GGG GAG CAG GGC CCC
 S   S   E   D   S   D   I   D   G   E   A   E   D   G   E   Q   G   P
```

FIGURE 2C

```
      1197            1206            1215            1224            1233            1242
ATC TGG ACG TTC CCC CCT ACC ATC CGG CCG AGT CCA CAC AGC AAG CTT CAC AAG
 I   W   T   F   P   P   T   I   R   P   S   P   H   S   K   L   H   K 1251            1260            1269            1278            1287            1296
GGG ACG GCC CTG CAC AGT TCA CAG AAG CCT GCG GAG CCC GTC AAG AGG CAG CCG
 G   T   A   L   H   S   S   Q   K   P   A   E   P   V   K   R   Q   P 1305            1314            1323            1332            1341            1350
AGG TCC CAG TGC CTG TCC ACG CTG GTC CGG CCC GTT TTC GGA GAG CTC AAG AGA
 R   S   Q   C   L   S   T   L   V   R   P   V   F   G   E   L   K   R 1359            1368            1377            1386            1395            1404
AGC ACA AGC AGA GCG GCG GGA GCG TGG GTG CGC TGG AGG AGC TGG AGA ACG CCT
 S   T   S   R   A   A   G   A   W   V   R   W   R   S   W   R   T   P 1413            1422            1431            1440            1449            1458
TCA GCC TGG CCG AGG AGT CCT GCC CCG GCA TCT CAG ACA AGC TGA TGG TGC ACC
 S   A   W   P   R   S   P   A   P   A   S   Q   T   S   *

1467            1476            1485            1494            1503            1512
TGG TGG AGC GAG TGC AGA GGT TTT CAC ACA GAA ACC ACC TGA CAT CCA CCC 1521            1530            1539            1548            1557            1566
GCT GAA GCG CAC TGC TGT TCA GAT AGG GGA CGG AAG GTC GTT TGT TTT TGT TCT
```

FIGURE 2D

```
      1575         1584         1593         1602         1611         1620
GAG CTC CAT  AAG AAC TGT  GCT GAC TTG  GAA GGT GCC  CTG TGC TAT  GTC GTG CCT 1629         1638         1647         1656         1665         1674
GCA GGG ACA  CGT CGG ATC  CCG TGG GCC  TCA CAT GCC  AGG TCA CCA  GGT CAC CGT 1683         1692         1701         1710         1719         1728
CTC CTT CCA  CCC CTG CAG  TGT GCT GTT  GTG CAC GTC  AGG GAC GCT  GTT CTC TAT 1737         1746         1755         1764         1773         1782
GCC CAC TGC  CCT CCC TCT  CCT GGC CCA  GCA GTA TTG  CTC ACG GGG  GCT CCA 1791         1800         1809         1818         1827         1836
GCC GGC GTG  GCC CTC ATG  AGC TAC GCC  TGG GTC TTC  TGC AGA CTC  ATG CAG 1845         1854         1863         1872         1881         1890
CCC TAT GGC  CGC TCA GAC  CAA GGC GCA  GAG CAA CTA  TCA GGG CAG  CTC TGC CTC 1899         1908         1917         1926         1935         1944
CTC CTC CCA TGA  GGT GGG GAG AGG CAA CAG GGC AGC CCC CAG AGG AGT GTC CTG 1953         1962         1971         1980         1989         1998
GCC GCT GTC CTC CCG GGG CCC ATG ATG GCC ATA GAT TTG CCT TGT GGT GTT GGA 2007         2016         2025         2034         2043         2052
TCA GGT ACT GTG TCT GCT CAT AAG TAC TTG TGT CAT CCA GAA TGT TTT GTT TTT
```

FIGURE 2E

```
2061      2070      2079      2088      2097      2106
TAA GAA AAT TGA ATT ACT TGT TTC CTG AAA TAT TCT GAG GTT AAT ATG TTA GTT
    2115      2124      2133      2142      2151      2160
TTC ATA GAA CAT TGA GAG GCC CCT GCC ACT TTC AAT AAA GAC CTG ACT TGG AGN

```
5' GCG GTG ATG GCG GTG AAA ACT GAG GCT GCT AAG GGC ACC CTC ACT TAC TCC
         9          18          27          36          45          54
       M   A   V   K   T   E   A   A   K   G   T   L   T   Y   S

AGG ATG AGG GGC ATG GTG GCA ATT CTC ATC GCT TTC ATG AAG CAG AGG AGG ATG
            63          72          81          90          99         108
     R   M   R   G   M   V   A   I   L   I   A   F   M   K   Q   R   R   M

GGT CTG AAC GAC TTT ATT CAG AAG ATT GCC AAT TCC TAT GCA TGC AAA CAC
           117         126         135         144         153         162
     G   L   N   D   F   I   Q   K   I   A   N   S   Y   A   C   K   H

CCT GAA GTT CAG TCC ATC TTG AAG ATC TCC CAA CCT CAG GAG CTT ATG
           171         180         189         198         207         216
     P   E   V   Q   S   I   L   K   I   S   Q   P   Q   E   L   M

AAT GCC AAC CCT TCT CCT CCA CCA AGT CCT TCT CAA CCT CAG CAA ATC AAC CTT GGC CCG
           225         234         243         252         261         270
     N   A   N   P   S   P   P   P   S   P   S   Q   P   Q   Q   I   N   L   G   P

TCG TCC AAT CCT CAT GCT AAA CCA TCT GAC TTT CAC TTC TTG AAA GTG ATC GGA
           279         288         297         306         315         324
     S   S   N   P   H   A   K   P   S   D   F   H   F   L   K   V   I   G

AAG GGC AGT TTT GGA AAG GTT CTT CTA GCA AGA CAC AAG GCA GAA GAA GTG TTC
           333         342         351         360         369         378
     K   G   S   F   G   K   V   L   L   A   R   H   K   A   E   E   V   F

FIGURE 3A
```

```
387                396           405           414           423           432
TAT GCA GTC AAA GTT TTA CAG AAG AAA GCA ATC CTG AAA AAG AAA GAG GAG AAG
 Y   A   V   K   V   L   Q   K   K   A   I   L   K   K   K   E   E   K 441                450           459           468           477           486
ATG TCG GAG CGG AAT GTT CTG TTG AAG AAT GTG AAG CAC CCT TTC CTG
CAT ATT                                                             
 H   I   M   S   E   R   N   V   L   L   K   N   V   K   H   P   F   L 495                504           513           522           531           540
GTG GGC CTT CAC TTC TCT TTC CAG ACT GCT GAC AAA TTG TAC TTT GTC CTA GAC
 V   G   L   H   F   S   F   Q   T   A   D   K   L   Y   F   V   L   D 549                558           567           576           585           594
TAC ATT AAT GGT GGA GAG TTG TTC TAC CAT CTC CAG AGG GAA TTG TAC CGC TGC TTC CTG
 Y   I   N   G   G   E   L   F   Y   H   L   Q   R   E   L   Y   R   C   F   L 603                612           621           630           639           648
GAA CCA CGG GCT CGT TCC TAT GCT GCT GAA ATA CAG AGG GAA AAT AGT GCC AGT GCC TTG GGC TAC CTG
 E   P   R   A   R   S   Y   A   A   E   I   Q   R   E   N   S   A   S   A   L   G   Y   L 657                666           675           684           693           702
CAT TCA CTG AAC ATC GTT TAT AGA GAC TTA AAA CCA GAG AAT ATT TTG CTA GAT
 H   S   L   N   I   V   Y   R   D   L   K   P   E   N   I   L   L   D 711                720           729           738           747           756
TCA CAG GGA CAC ATT GTC CTT ACT GAC TTC GGA CTC TGC AAG CTC GAG AAC ATT GAA
 S   Q   G   H   I   V   L   T   D   F   G   L   C   K   L   E   N   I   E
```

FIGURE 3B

```
765              774              783              792              801              810
CAC AAC AGC ACA ACA TCC ACC TTC TGT GGC ACG GAG TAT CTC GCA CCT GAG
 H   N   S   T   T   S   T   F   C   G   T   E   Y   L   A   P   E 819              828              837              846              855              864
GTG CTT CAT AAG CAG CCT TAT GAC AGG ACT GTG GAC TGG TGC CTG GGA GCT
 V   L   H   K   Q   P   Y   D   R   T   V   D   W   C   L   G   A 873              882              891              900              909              918
GTC TTG TAT GAG ATG CTG TAT GGC CTG CCG CCT TTT TAT AGC TGC CGA AAC ACA GCT
 V   L   Y   E   M   L   Y   G   L   P   P   F   Y   S   C   R   N   T   A 927              936              945              954              963              972
GAA ATG TAC GAC AAC ATT CTG AAC AAG CCT CTC CAG CTG AAA CCA AAT ATT ACA
 E   M   Y   D   N   I   L   N   K   P   L   Q   L   K   P   N   I   T 981              990              999              1008             1017             1026
AAT TCC GCA AGA CAC CTC CTG GAG GGC CTC CTG CAG AAG GAC AGG ACA AAG CGG
 N   S   A   R   H   L   L   E   G   L   L   Q   K   D   R   T   K   R 1035             1044             1053             1062             1071             1080
CTC GGG GCC AAG GAT GAC TTC ATG GAG ATT AAG AGT CAT GTC TTC TTC TCC TTA
 L   G   A   K   D   D   F   M   E   I   K   S   H   V   F   F   S   L 1089             1098             1107             1116             1125             1134
ATT AAC TGG GAT GAT CTC ATT AAT AAG AAG ATT ACT CCC CCT TTT AAC CCA AAT
 I   N   W   D   D   L   I   N   K   K   I   T   P   P   F   N   P   N
```

FIGURE 3C

```
      1143            1152            1161            1170            1179            1188
GTG AGT GGG CCC AAC GAC CTA CGG CAC TTT GAC CCC GAG TTT ACC GAA GAG CCT
 V   S   G   P   N   D   L   R   H   F   D   P   E   F   T   E   E   P 1197            1206            1215            1224            1233            1242
GTC CCC AAC TCC ATT GGC AAG TCC CCT GAC AGC GTC CTC GTC ACA GCC AGC GTC
 V   P   N   S   I   G   K   S   P   D   S   V   L   V   T   A   S   V 1251            1260            1269            1278            1287            1296
AAG GAA GCT GCC GAG GCT TTC CTA GGC TTT TCC TAT GCG CCT CCC ACG GAC TCT
 K   E   A   A   E   A   F   L   G   F   S   Y   A   P   P   T   D   S 1305            1314            1323            1332            1341            1350
TTC CTC TGA ACC CTG TTA GGG CTT GGT TTT AAA GGA TTT TAT GTG TGT TTC CGA
 F   L 1359            1368            1377            1386            1395            1404
ATG TTT TAG TTA GCC TTT TGG TGG AGC CGC CAG ACA GGA CAT CTT ACA AGA 1413            1422            1431            1440            1449            1458
GAA TTT GCA CAT CTC TGG AAG CTT AGC AAT CTT ATT GCA CAC TGT TCG CTG GAA 1467            1476            1485            1494            1503            1512
GCT TTT TGA AGA GCA CAT TCT CCT CAG TGA GCT CAT GAG GTT TTC ATT TTT ATT 1521            1530            1539            1548            1557            1566
CTT CCT TCC AAC GTG GTG CTA TCT CTG AAA CGA GCG TTA GAG TGC CGC CTT AGA
```

FIGURE 3D

```
        1575            1584            1593            1602            1611            1620
CGG AGG CAG GAG TTT CGT TAG AAA GCG GAC GCT GTT CTA AAA AAG GTC TCC TGC 1629            1638            1647            1656            1665            1674
AGA TCT GTC TGG GCT GTG ATG ACG AAT ATT ATG AAA TGT GCC TTT TCT GAA GAA 1683            1692            1701            1710            1719            1728
AAT TGT GTT AGC TCC AAA GCT TTT CCT ATC GCA GTG TTT CAG TTC TTT ATT TTC 1737            1746            1755            1764            1773            1782
CCT TGT GGA TAT GCT GTG TGA ACC GTC GTG TGA GTG TGG TAT GCC TGA TCA CAG 1791            1800            1809            1818            1827            1836
ATG GAT TTT GTT ATA AGC ATC AAT GTG ACA CTT GCA GGA CAC TAC AAC GTG GGA 1845            1854            1863            1872            1881            1890
CAT TGT TTG TTT CTT CCA TAT TTG GAA GAT AAA TTT ATG TGT AGA CTT TTT TGT 1899            1908            1917            1926            1935            1944
AAG ATA CGG TTA ATA ACT AAA ATT TAT TGA AAT GGT CTT GCA ATG ACT CGT ATT 1953            1962            1971            1980            1989            1998
CAG ATG CTT AAA GAA AGC ATT GCT ACA AAT ATT TCT ATT TTT AGA AAG GGT 2007            2016            2025            2034            2043            2052
TTT TAT GGA CCA ATG CCC CAG TTG TCA GTC AGA GCC GTT GGT GTT TTT CAT TGT
```

FIGURE 3E

```
                         2061         2070         2079         2088         2097              2106
                  TTA AAA TGT CAC CTG TAA AAT GGG CAT TAT TTA TGT TTT TTT TGC ATT CCT
                         2115         2124         2133         2142         2151              2160
                  GAT AAT TGT ATG TAT TGT ATA AAG AAC GTC TGT ACA TTG GGT TAT AAC ACT AGT
                         2169         2178         2187         2196         2205              2214
                  ATA TTT AAA CTT ACA GGC TTA TTT GTA ATG TAA ACC ACC ATT TTA ATG TAC TGT
                         2223         2232         2241         2250         2259              2268
                  AAT TAA CAT GGT TAT AAT ACG NAC AAT CCT TCC CTC ATC CCA TCA CAC AAC TTT
                         2277         2286         2295         2304
                  TTT TGT GTG TGA TAA ACT GAT TTT GGT TTG CAA TAA AAC CTT G 3'
```

```
221 Q V A K Q M H - - - I - - - - - - - - - - - W M S S X - - - - - - - - -          HPK-1
367 - - - G E L K R S T S R A A G A W V R W R S W R T P - - - - - - - S A W P        HPK-2
375 N V S G P N D L R H F D P E F T E E P V P N S I G K S P D S - - - V L V T A S    HPK-3
223 K L Q N D Q R P V K F Y - - - - - - - - - - R F V P R                             GI 1082115
401 Q K E K E N Q I N S F G K S V P G P L K N S S D W K I P Q D G D Y E F L K S W T  GI 1117791
374 N V S G P S D L R H F D P E F T E E P V P S S I G R S P D S - - - I L V T A S    GI 294637

233 - - - - - - - - - - - - - - - - - - - - - - - - - - - - - -                      HPK-1
394 - - - - - - - - - - - - - - - - - - - - - - - - - - - R S P A P A S              HPK-2
411 V K E A A E A F L G F S - -                                                       HPK-3
239 - - - - - - - - - - - - - - - - - - - - - - - - - - Y A P P T D S F L            GI 1082115
441 V E D L Q K R L L A L D P M M E Q E I E E I R Q K Y Q S K R Q P I L D A I E A K   GI 1117791
410 V K E A A E A F L G F S - -                                   Y A P P M D S F L  GI 294637

233 - - - - Q T S                HPK-1
401                              HPK-2
431                              HPK-3
239                              GI 1082115
481 K R R Q Q N F                GI 1117791
430                              GI 294637
```

FIGURE 4D

HUMAN PROTEIN KINASES

FIELD OF THE INVENTION

The present invention relates to nucleic acid and amino acid sequences of novel human protein kinases and to the use of these sequences in the diagnosis, study, prevention and treatment of disease.

BACKGROUND OF THE INVENTION

Kinases regulate many different cell proliferation, differentiation, and signalling processes by adding phosphate groups to proteins. Uncontrolled signalling has been implicated in a variety of disease conditions including, inflammation, cancer, arteriosclerosis, and psoriasis. Reversible protein phosphorylation is the main strategy for controlling activities of eukaryotic cells. It is estimated that more than 1000 of the 10,000 proteins active in a typical mammalian cell are phosphorylated. The high energy phosphate which drives activation is generally transferred from adenosine triphosphate molecules (ATP) to a particular protein by protein kinases and removed from that protein by protein phosphatases.

Phosphorylation occurs in response to extracellular signals (hormones, neurotransmitters, growth and differentiation factors, etc), cell cycle checkpoints, and environmental or nutritional stresses and is roughly analogous to turning on a molecular switch. When the switch goes on, the appropriate protein kinase activates a metabolic enzyme, regulatory protein, receptor, cytoskeletal protein, ion channel or pump, or transcription factor.

The kinases comprise the largest known protein group, a superfamily of enzymes with widely varied functions and specificities. They are usually named after their substrate, their regulatory molecules, or some aspect of a mutant phenotype. Almost all kinases contain a similar 250-300 amino acid catalytic domain. The N-terminal domain, which contains subdomains I-IV, generally folds into a two-lobed structure which binds and orients the ATP (or GTP) donor molecule. The larger C terminal lobe, which contains subdomains VI A–XI, binds the protein substrate and carries out the transfer of the gamma phosphate from ATP to the hydroxyl group of a serine, threonine, or tyrosine residue. Subdomain V spans the two lobes.

The kinases may be categorized into families by the different amino acid sequences (generally between 5 and 100 residues) located on either side of, or inserted into loops of, the kinase domain. These added amino acid sequences allow the regulation of each kinase as it recognizes and interacts with its target protein. The primary structure of the kinase domains is conserved and can be further subdivided into 11 subdomains. Each of the 11 subdomains contain specific residues and motifs or patterns of amino acids that are characteristic of that subdomain and are highly conserved (Hardie G and Hanks S (1995) The Protein Kinase Facts Books, I and II, Academic Press, San Diego Calif.).

The second messenger dependent protein kinases primarily mediate the effects of second messengers such as cyclic AMP (cAMP) cyclic GMP, inositol triphosphate, phosphatidylinositol, 3,4,5-triphosphate, cyclic ADPribose, arachidonic acid and diacylglycerol. Cyclic-AMP is an intracellular mediator of hormone action in all procaryotic and animal cells that have been studied. Such hormone-induced cellular responses include thyroid hormone secretion, cortisol secretion, progesterone secretion, glycogen breakdown, bone resorption, and regulation of heart rate and force of heart muscle contraction. Cyclic AMP-dependent protein kinase (PKA) is found in all animal cells and is thought to account for the all of the effects of cyclic-AMP in most of these cells. In its inactive state, A-kinase consists of a complex of two catalytic subunits and two regulatory subunits. When each regulatory subunit has bound two molecules of cAMP, the catalytic subunit is activated and can transfer a high energy phosphate from ATP to the serine or threonine of a substrate protein. Altered PKA expression is implicated in a variety of disorders and diseases including; thyroid disorders, diabetes, atherosclerosis, and cardiovascular disease (Isselbacher K J et al (1994) Harrison's Principles of Internal Medicine, McGraw-Hill, New York City).

Protein kinase C (PKC) is a water-soluble, $Ca^{++}$-dependent kinase, commonly found in brain tissue, which moves to the plasma membrane in the presence of $Ca^{++}$ ions. Approximately half of the known isoforms of PKC are activated initially by diacylglycerol and phosphatidylserine. Prolonged activation of PKC depends on continued production of diacyglycerol molecules which are formed when phospholipases cleave phosphatidylcholine. In nerve cells, PKC phosphorylates ion channels and alters the excitability of the cell membrane. In other cells, activation of PKC increases gene transcription either by triggering a protein kinase cascade which activates a regulatory element or by phosphorylating and deactivating an inhibitor of the regulatory protein. PKC activity has been specifically linked to multi-drug resistance in cancer (O'Brian C A et al (1995) Prog Clin Biol Res 391: 117–120), tumor promotion (O'Brian C A and Ward N E (1989) Cancer Metast Rev 8: 199–214) memory disorders (Saito N. et al (1994) Brain Res 656: 245–256), and auto-immune disease (Ohkusu K et al (1995) Eur J Immunol 25: 3180–3186).

A detailed understanding of kinase pathways and signal transduction is beginning to reveal some mechanisms for interceding in the progression of inflammatory illnesses and of uncontrolled cell proliferation. The novel kinases, polynucleotides which encode them, and antibodies to them satisfy a need in the art by providing a plurality of tools for studying signalling cascades in various cells and tissues, diagnosing disease and selecting inhibitors or drugs with the potential to intervene in various disorders or diseases in which altered kinase expression is implicated.

SUMMARY OF THE INVENTION

The present invention is directed to three novel human protein kinases (hereinafter referred to individually as HPK1, HPK2, and HPK3, and collectively as HPK) characterized as having homology to other protein kinases. Accordingly, the invention features substantially purified HPK, comprising the amino acid sequences of SEQ ID Nos:1, 3, and 5, or fragments thereof and having functional characteristics of protein kinase family members.

One aspect of the invention features isolated polynucleotides which encode all or a part of HPK. In a particular aspect, the polynucleotides are the nucleotide sequences shown in SEQ ID NOs:2, 4, and 6. Also provided are vectors containing such polynucleotides and host cells transformed or transfected with such vectors.

The invention further relates to poylynucleotide sequences complementary to the polynucleotides encoding HPK or variants thereof, antibodies or antagonists to HPK, and pharmaceutical compositions comprising HPK or antagonists to HPK.

BRIEF DESCRIPTION OF THE FIGURES

FIGS. 1A, 1B, 1C, and 1D show the nucleic acid sequence (SEQ ID NO:2) and amino acid sequence (SEQ ID NO:1) of the human protein kinase, HPK-1. The alignment was produced using MACDNASIS software (Hitachi Software Engineering Co Ltd, San Bruno, Calif.).

FIGS. 2A, 2B, 2C, 2D, 2E, and 2F show the nucleic acid sequence (SEQ ID NO:4) and amino acid sequence (SEQ ID NO:3) of the human protein kinase, HPK-2.

FIGS. 3A, 3B, 3C, 3D, 3E, and 3F show the nucleic acid sequence (SEQ ID NO:6) and amino acid sequence (SEQ ID NO:5) of the human protein kinase, HPK-3.

FIGS. 4A, 4B, 4C, and 4D show the amino acid sequence alignments between HPK-1, HPK-2, HPK-3 and protein kinases from the nematode, *C. elegans* (GI 1082115; SEQ ID NO:7), a human protein kinase (GI 1117791; SEQ ID NO:8), and a protein kinase from rat (GI 294637; SEQ ID NO:9). The alignments were produced using the multisequence alignment program of DNASTAR software (DNAStar Inc, Madison Wis.).

DETAILED DESCRIPTION OF THE INVENTION

Before the present nucleotide and polypeptide sequences are described, it is to be understood that this invention is not limited to the particular methodology, protocols, cell lines, vectors and reagents described as such may, of course, vary. It is also to be understood that the terminology used herein is for the purpose of describing particular embodiments only, and is not intended to limit the scope of the present invention which will be limited only by the appended claims.

It must be noted that as used herein and in the appended claims, the singular forms of "a", "and", and "the" include plural referents unless the context clearly dictates otherwise. Thus, for example, reference to "a host cell" includes a plurality of such host cells and reference to "the antibody" includes reference to one or more antibodies and equivalents thereof known to those skilled in the arts, and so forth.

Unless defined otherwise, all technical and scientific terms used herein have the same meaning as commonly understood to one of ordinary skill in the art to which this invention belongs. Although any methods, devices and materials similar or equivalent to those described herein can be used in the practice of testing of the invention, the preferred methods, devices and materials are now described.

All publications mentioned herein are incorporated herein by reference for the purpose of describing and disclosing the cell lines, vectors, and methodologies which are described in the publications which might be used in connection with the presently described invention. The publications discussed herein are provided solely for their disclosure prior to the filing date of the present application. Nothing herein is to be construed as an admission that the inventors are not entitled to antedate such disclosure by virtue of prior invention.

Definitions

"Nucleic acid sequence" as used herein refers to an oligonucleotide, nucleotide or polynucleotide, and fragments or portions thereof, and to DNA or RNA of genomic or synthetic origin which may be single- or double-stranded, and represent the sense or antisense strand. Similarly, amino acid sequence as used herein refers to protein or peptide sequence.

"Consensus" as used herein may refer to a nucleic sequence 1) which has been resequenced to resolve uncalled bases, 2) which has been extended using XL-PCR (Perkin Elmer) in the 5' or the 3' direction and resequenced, 3) which has been assembled from overlapping sequences of more than one Incyte clone GCG Fragment Assembly System, (GCG, Madison Wis.), or 4) which has been both extended and assembled.

"Peptide nucleic acid" as used herein refers to a molecule which comprises an oligomer to which an amino acid residue, such as lysine, and an amino group have been added. These small molecules, also designated anti-gene agents, stop transcript elongation by binding to their complementary (template) strand of nucleic acid (Nielsen P E et al (1993) Anticancer Drug Des 8:53–63).

As used herein, HPK refers to the amino acid sequence of substantially purified HPK from any source whether natural, synthetic, semi-synthetic or recombinant.

A "variant" of HPK is defined as an amino acid sequence that is different by one or more amino acid substitutions. The variant may have "conservative" changes, wherein a substituted amino acid has similar structural or chemical properties, eg, replacement of leucine with isoleucine. More rarely, a variant may have "nonconservative" changes, eg, replacement of a glycine with a tryptophan. Similar minor variations may also include amino acid deletions or insertions, or both. Guidance in determining which and how many amino acid residues may be substituted, inserted or deleted without abolishing biological or immunological activity may be found using computer programs well known in the art, for example, DNASTAR software.

A "deletion" is defined as a change in either nucleotide or amino acid sequence in which one or more nucleotides or amino acid residues, respectively, are absent.

An "insertion" or "addition" is that change in a nucleotide or amino acid sequence which has resulted in the addition of one or more nucleotides or amino acid residues, respectively, as compared to the naturally occurring HPK.

A "substitution" results from the replacement of one or more nucleotides or amino acids by different nucleotides or amino acids, respectively.

The term "biologically active" refers to a HPK having structural, regulatory or biochemical functions of the naturally occurring HPK. Likewise, "immunologically active" defines the capability of the natural, recombinant or synthetic HPK, or any oligopeptide thereof, to induce a specific immune response in appropriate animals or cells and to bind with specific antibodies.

The term "derivative" as used herein refers to the chemical modification of a nucleic acid sequence encoding HPK or the encoded HPK. Illustrative of such modifications would be replacement of hydrogen by an alkyl, acyl, or amino group. A nucleic acid derivative would encode a polypeptide which retains essential biological characteristics of natural HPK.

As used herein, the term "substantially purified" refers to molecules, either nucleic or amino acid sequences, that are removed from their natural environment, isolated or separated, and are at least 60% free, preferably 75% free, and most preferably 90% free from other components with which they are naturally associated.

"Stringency" typically occurs in a range from about Tm–5° C. (5° C. below the Tm of the probe)to about 20° C. to 25° C. below Tm. As will be understood by those of skill in the art, a stringency hybridization can be used to identify or detect identical polynucleotide sequences or to identify or detect similar or related polynucleotide sequences.

The term "hybridization" as used herein shall include "any process by which a strand of nucleic acid joins with a complementary strand through base pairing" (Coombs J (1994) *Dictionary of Biotechnology*, Stockton Press, New York N.Y.). Amplification as carried out in the polymerase chain reaction technologies is described in Dieffenbach C W and G S Dveksler (1995, *PCR Primer, a Laboratory Manual*, Cold Spring Harbor Press, Plainview N.Y.).

Description

The present invention relates to novel human protein kinases, HPK, initially identified among the partial cDNAs from a brain hippocampus library (HIPONOTO1; HPK-1), a peripheral blood mononuclear cell library (TMLR3DT01; HPK-2) and a macrophage cell library (MPHGN0T03; HPK-3) and to the use of the nucleic acid and amino acid sequences disclosed herein in the study, diagnosis, prevention and treatment of disease.

In addition to the above mentioned sources, northern analysis indicates that nucleic acid encoding a portion of HPK-1 was also found in cDNA libraries from neural tissue (multiple sclerosis) and brain tumor. Nucleic acid encoding portions of HPK-2 was found in infant brain, epilepsy (brain) and various tumor tissues (penis carcinoma, bladder carcinoma, and thyroid adenoma). Nucleic acid encoding portions of HPK-3 was found in multiple sclerosis, Alzheimers (brain), osteoarthritic knee tissue, and in tumors of the breast and lung.

The present invention also encompasses HPK variants. A preferred HPK variant is one having at least 80% amino acid sequence similarity to the HPK amino acid sequences (SEQ ID NO:1, 3, or 5), a more preferred HPK variant is one having at least 90% amino acid sequence similarity to SEQ ID NO:1, 3, or 5, and a most preferred HPK variant is one having at least 95% amino acid sequence similarity to SEQ ID NO:1, 3, or 5.

The HPK Coding Sequences

Nucleic acid encoding a portion of HPK-1 was first identified in the cDNA, Incyte Clone 240142, through a computer-generated search for amino acid sequence alignments. Similarly, nucleic acids encoding a portion of HPK-2 and HPK-3 were first identified in Incyte Clones 391602 and 477245, respectively. The nucleic acid sequences, SEQ ID NO:2, 4, and 6; disclosed herein encode the amino acid sequences, SEQ ID NO:1, 3, and 5, respectively, disclosed hereinafter as HPK.

The present invention is based, in part, on the chemical and structural homology among HPK-1, -2, and -3, and various known protein kinases, and to various amino acid sequence motifs within these proteins that are characteristic of the catalytic domains of protein kinases (Hardie G and Hanks S (1995), supra). Referring to FIGS. 4A, 4B, 4C, and 4D, the sequence GXGXXGXV characteristic of subdomain I in protein kinases is found in HPK-2 beginning at $G_{27}$ and in the corresponding residues for HPK-3, GI 1117791, and GI 294637. The conserved lysine residue in subdomain II located at $K_{49}$ for HPK-2 is repeated for HPK-3, GI 1117791, and GI 294637. The sequence HRDIKXXN found in subdomain VI B of many protein kinases is found in HPK-1($H_{90}$), HPK-2, HPK-3, GI 1082115 and GI 1117791. Finally, the triplet sequence DFG in subdomain VII is found in HPK-3 ($G_{242}$), GI 1117791, and GI 294637, and the triplet sequence APE (subdomain VIII) is found in HPK-2 ($A_{283}$), HPK-3, GI 1117791, and GI 294637.

Thus each of the protein kinases HPK-1, -2, and -3 bear sequence patterns characteristic of protein kinases, but are distinct from one another in overall sequence. HPK-1 bears 70% sequence identity to a protein kinase from the nematode, C. elegans; GI 1082115 (Wilson, R et al (1994) Nature 368: 32–38). GI 1082115 has been characterized as a member of the cyclic-AMP dependent PKA family. HPK-2 bears closest identity (42%)to a human protein kinase; GI 1117791 (Creasy, C L and Chernoff, J (1995) J. Biol Chem 270: 21695–21700). GI 1117791 is characterized as being similar to other members of the mitogen-activated protein kinase (MAPK) family but is most likely involved in an as yet unidentified signal transduction pathway. HPK-3 has approximately 96% identity to a protein kinase from rat; GI 294637 (Webster, M. K. et al (1993) Mol. Cell Biol. 13: 2031–2040). GI 294637 is transcriptionally regulated by glucocorticoid hormones and bears sequence homology to protein kinases of both the PKA and PKC families.

HPK-1 is encoded by SEQ ID NO:2 and is derived from the extension and assembly of the following partial cDNAs (library), Incyte Clones 67192(HUVESTB01); 240142, 243638, and 298165(HIPONOT01); 449634 (TLYMNOT02); 461400(KERANOT01); 739131 (PANCNOT04); and (12143028?).

HPK-2 is encoded by SEQ ID NO:4 and is derived from the extension and assembly of the following partial cDNAs, Incyte Clones 1394374, 1395924, 1392440, 1394764, 1393587, and 1439946(THYRNOT03; 487890 (HNT2AGT01); 737620(TONSNOT01); 391602 (TMLR3DT01); 373301(LUNGNOT02); 1291632 (PGANNOT03); 550890(BEPINOT01); 1314539 (BLADTUT02); 647351(BRSTTUT02); 917302 (BRSTNOT04), 541117(LNODNOT02); 235796 (SINTNOT02); 827973(PROSNOT06); 36252 (HUVENOB01); 1339623(COLNTUT03); 719820 and 365833(SYNORAT01); 32632(THP1NOB01); 888061 (PANCNOT05); 1262882(SYNORAT05); 975808 (MUSCNOT02); 275375(TESTNOT03);1433039 and 1425069(BEPINON01);and 94156(PITUNOT01).

HPK-3 is encoded by SEQ ID NO:6 and is derived from the extension and assembly of the following partial cDNAs, Incyte Clones 477245 and 445652(MPHGNOT03); 386314 (THYMNOT02); 1219404(NEUTGMT01); 478857 (MMLR2DT01); 1239468(LUNGTUT02); 603976 (BRSTTUT01; and 565613(NEUTLPT01).

It will be appreciated by those skilled in the art that as a result of the degeneracy of the genetic code, a multitude of HPK-encoding nucleotide sequences, some bearing minimal homology to the nucleotide sequences of any known and naturally occurring gene may be produced. The invention contemplates each and every possible variation of nucleotide sequence that could be made by selecting combinations based on possible codon choices. These combinations are made in accordance with the standard triplet genetic code as applied to the nucleotide sequence of naturally occurring HPK, and all such variations are to be considered as being specifically disclosed.

Although nucleotide sequences which encode HPK and its variants are preferably capable of hybridizing to the nucleotide sequence of the naturally occurring HPK under appropriately selected conditions of stringency, it may be advantageous to produce nucleotide sequences encoding HPK or its derivatives possessing a substantially different codon usage. Codons may be selected to increase the rate at which expression of the peptide occurs in a particular prokaryotic or eukaryotic expression host in accordance with the frequency with which particular codons are utilized by the host. Other reasons for substantially altering the nucleotide sequence encoding HPK and its derivatives without altering the encoded amino acid sequences include the production of RNA transcripts having more desirable properties, such as a greater half-life, than transcripts produced from the naturally occurring sequence.

It is now possible to produce a DNA sequence, or portions thereof, encoding any of the claimed HPK and derivatives, entirely by synthetic chemistry, after which the synthetic gene may be inserted into any of the many available DNA vectors and cell systems using reagents that are well known in the art at the time of the filing of this application.

Moreover, synthetic chemistry may be used to introduce mutations into a HPK sequence or any portion thereof.

Also included within the scope of the present invention are polynucleotide sequences that are capable of hybridizing to the nucleotide sequence of FIGS. 1A, 1B, 1C, and 1D under various conditions of stringency. Hybridization conditions are based on the melting temperature (Tm) of the nucleic acid binding complex or probe, as taught in Berger and Kimmel (1987, *Guide to Molecular Cloning Techniques, Methods in Enzymology*, Vol 152, Academic Press, San Diego Calif.) incorporated herein by reference, and may be used at a defined stringency.

Altered nucleic acid sequences encoding HPK which may be used in accordance with the invention include deletions, insertions or substitutions of different nucleotides resulting in a polynucleotide that encodes the same or a functionally equivalent HPK. The protein may also show deletions, insertions or substitutions of amino acid residues which produce a silent change and result in a functionally equivalent HPK. Deliberate amino acid substitutions may be made on the basis of similarity in polarity, charge, solubility, hydrophobicity, hydrophilicity, and/or the amphipathic nature of the residues as long as the biological activity of HPK is retained. For example, negatively charged amino acids include aspartic acid and glutamic acid; positively charged amino acids include lysine and arginine; and amino acids with uncharged polar head groups having similar hydrophilicity values include leucine, isoleucine, valine; glycine, alanine; asparagine, glutamine; serine, threonine phenylalanine, and tyrosine.

Included within the scope of the present invention are alleles of HPK encoding sequences. As used herein, an "allele" or "allelic sequence" is an alternative form of an HPK encoding sequence. Alleles result from a mutation, for example, a change in the nucleic acid sequence, and generally produce altered mRNAs or polypeptides whose structure or function may or may not be altered. Any given gene may have, one or many allelic forms, or none at all. Common mutational changes which give rise to alleles are generally ascribed to natural deletions, additions or substitutions of amino acids. Each of these types of changes may occur alone, or in combination with the others, one or more times in a given sequence.

Methods for DNA sequencing which are well known in the art may be used and these methods may employ such enzymes as the Klenow fragment of DNA polymerase I, SEQUENASE® (US Biochemical Corp, Cleveland Ohio)), Taq polymerase (Perkin Elmer, Norwalk Conn.), thermostable T7 polymerase (Amersham, Chicago Ill.), or combinations of recombinant polymerases and proofreading exonucleases such as the ELONGASE Amplification System marketed by Gibco BRL (Gaithersburg Md.). Preferably, the process is automated with machines such as the Hamilton Micro Lab 2200 (Hamilton, Reno Nev.), Peltier Thermal Cycler (PTC200; M J Research, Watertown Mass.) and the ABI 377 DNA sequencers (Perkin Elmer).

Extending the Polynucleotide Sequence

The polynucleotide sequence encoding HPK may be extended utilizing partial nucleotide sequence and various methods known in the art to detect upstream sequences such as promoters and regulatory elements. For example, one may use "restriction-site" polymerase chain reaction (PCR) as a direct method which uses universal primers to retrieve an unknown sequence adjacent to a known locus (Gobinda et al (1993) PCR Methods Applic 2:318–22). In particular, the genomic DNA is amplified in the presence of primer to a linker sequence and a primer specific to the known region.

The amplified sequences are subjected to a second round of PCR with the same linker primer and another specific primer internal to the first one. Products of each round of PCR are transcribed with an appropriate RNA polymerase and sequenced using reverse transcriptase.

Inverse PCR can be used to amplify or extend sequences using divergent primers based on a known region (Triglia T et al (1988) Nucleic Acids Res 16:8186). The primers may be designed using OLIGO® 4.06 Primer Analysis Software (1992; National Biosciences Inc, Plymouth Minn.), or another appropriate program, to be 22–30 nucleotides in length, to have a GC content of 50% or more, and to anneal to the target sequence at temperatures about 68°–72° C. The method uses several restriction enzymes to generate a suitable fragment in the known region of a gene. The fragment is then circularized by intramolecular ligation and used as a PCR template.

Another method which may be used is capture PCR (Lagerstrom M et al (1991) PCR Methods Applic 1:111–19) which involves PCR amplification of DNA fragments adjacent to a known sequence in human and yeast artificial chromosome DNA. Capture PCR involves multiple restriction enzyme digestions and ligations to place an engineered double-stranded sequence into an unknown portion of the DNA molecule before PCR.

Another method which may be used to retrieve unknown sequences is that of (Parker J D et al (1991; Nucleic Acids Res 19:3055–60). Additionally, one can use PCR, nested primers and PROMOTERFINDER™ libraries to walk in genomic DNA (PROMOTERFINDER™ Clontech ,Palo Alto Calif.). This process avoids the need to screen libraries and is useful in finding intron/exon junctions. Preferred libraries for screening for full length cDNAs are those that have been size-selected to include larger cDNAs. Also, random primed libraries are preferred in that they will contain more sequences which contain the 5' and upstream regions of genes. A randomly primed library may be particularly useful if an oligo d(T) library does not yield a full-length cDNA. Genomic libraries are useful for extension into the 5' nontranslated regulatory region.

Capillary electrophoresis may be used to analyze the size or confirm the nucleotide sequence of sequencing or PCR products. Systems for rapid sequencing are available from Perkin Elmer, Beckman Instruments (Fullerton Calif.), and other companies. Capillary sequencing may employ flowable polymers for electrophoretic separation, four different fluorescent dyes (one for each nucleotide) which are laser activated, and detection of the emitted wavelengths by a charge coupled device camera. Output/light intensity is converted to an electrical signal using appropriate software (eg. GENOTYPER and SEQUENCE NAVIGATOR™ from Perkin Elmer) and the entire process from loading of samples to computer analysis and electronic data display is computer controlled. Capillary electrophoresis is particularly suited to the sequencing of small pieces of DNA which might be present in limited amounts in a particular sample. The reproducible sequencing of up to 350 bp of M13 phage DNA in 30 min has been reported (Ruiz-Martinez M C et al (1993) Anal Chem 65:2851–8).

Expression of the Nucleotide and Protein Sequences

In accordance with the present invention, polynucleotide sequences which encode HPK, fragments of the polypeptide, fusion proteins or functional equivalents thereof may be used in recombinant DNA molecules that direct the expression of HPK in appropriate host cells. Due to the inherent degeneracy of the genetic code, other DNA sequences which encode substantially the same or a functionally equivalent amino acid sequence, may be used to clone and express HPK. As will be understood by those of skill in the art, it may be advantageous to produce HPK-encoding nucleotide sequences possessing non-naturally occurring codons. Codons preferred by a particular prokaryotic or eukaryotic host can be selected, for example, to increase the rate of HPK encoding sequences expression or to produce recombinant RNA transcripts having desirable properties, such as a longer half-life, than transcripts produced from naturally occurring sequence (Murray E et al (1989) Nuc Acids Res 17:477–508).

The nucleotide sequences of the present invention can be engineered in order to alter HPK encoding sequences for a variety of reasons, including but not limited to, alterations which modify the cloning, processing and/or expression of the gene product. For example, mutations may be introduced using techniques which are well known in the art. For example, site-directed mutagenesis may be used to insert new restriction sites, alter glycosylation patterns, change codon preference, produce splice variants, and so forth.

In another embodiment of the invention, a natural, modified or recombinant sequence encoding HPK may be ligated to a heterologous sequence to encode a fusion protein. For example, for screening of peptide libraries for inhibitors of HPK activity, it may be useful to encode a chimeric HPK protein that is recognized by a commercially available antibody. A fusion protein may also be engineered to contain a cleavage site located between a HPK sequence and the heterologous protein sequence, so that the HPK may be cleaved and substantially purified away from the heterologous moiety.

In an alternate embodiment of the invention, the sequence encoding HPK may be synthesized, whole or in part, using chemical methods well known in the art (see Caruthers M H et al (1980) Nuc Acids Res Symp Ser 215–23, Horn T et al(1980) Nuc Acids Res Symp Ser 225–32, etc). Alternatively, the proteins may be produced using chemical methods to synthesize amino acid sequences, whole or in part. For example, peptide synthesis can be performed using various solid-phase techniques (Roberge J Y et al (1995) Science 269:202–204) and automated synthesis may be achieved, for example, using the ABI 431A Peptide Synthesizer (Perkin Elmer) in accordance with the instructions provided by the manufacturer.

The newly synthesized peptide can be substantially purified by preparative high performance liquid chromatography (eg, Creighton (1983) *Proteins, Structures and Molecular Principles*, W H Freeman and Co, New York N.Y.). The composition of the synthetic peptides may be confirmed by amino acid analysis or sequencing (eg, the Edman degradation procedure; Creighton, supra). Additionally the amino acid sequence of HPK, or any part thereof, may be altered during direct synthesis and/or combined using chemical methods with sequences from other proteins, or any part thereof, to produce a variant polypeptide.

Expression Systems

In order to express a biologically active HPK, the nucleotide sequence encoding HPK or its functional equivalent, is inserted into an appropriate expression vector, ie, a vector which contains the necessary elements for the transcription and translation of the inserted coding sequence.

Methods which are well known to those skilled in the art can be used to construct expression vectors containing a HPK coding sequence and appropriate transcriptional or translational controls. These methods include in vitro recombinant DNA techniques, synthetic techniques and in vivo recombination or genetic recombination. Such techniques are described in Sambrook et al (1989) *Molecular Cloning, A Laboratory Manual*, Cold Spring Harbor Press, Plainview N.Y. and Ausubel F M et al (1989) *Current Protocols in Molecular Biology*, John Wiley & Sons, New York N.Y.

A variety of expression vector/host systems may be utilized to contain and express a HPK coding sequence. These include but are not limited to, microorganisms such as bacteria transformed with recombinant bacteriophage, plasmid or cosmid DNA expression vectors; yeast transformed with yeast expression vectors; insect cell systems infected with virus expression vectors (eg, baculovirus); plant cell systems transfected with virus expression vectors (eg, cauliflower mosaic virus, CaMV; tobacco mosaic virus, TMV) or transformed with bacterial expression vectors (eg, Ti or pBR322 plasmid); or animal cell systems.

The "control elements" or "regulatory sequences" of these systems may vary in their strength and specificities and are those nontranslated regions of the vector, enhancers, promoters, and 3' untranslated regions, which interact with host cellular proteins to carry out transcription and translation. Depending on the vector system and host utilized, any number of suitable transcription and translation elements, including constitutive and inducible promoters, may be used. For example, when cloning in bacterial systems, inducible promoters such as the hybrid lacZ promoter of the BLUESCRIPT® phagemid (Stratagene, LaJolla Calif.) or PSPORT1 (Gibco BRL) and ptrp-lac hybrids and the like may be used. The baculovirus polyhedrin promoter may be used in insect cells. Promoters or enhancers derived from the genomes of plant cells (eg, heat shock, RUBISCO; and storage protein genes) or from plant viruses (eg, viral promoters or leader sequences) may be cloned into the vector. In mammalian cell systems, promoters from the mammalian genes or from mammalian viruses are most appropriate. If it is necessary to generate a cell line that contains multiple copies of HPK encoding sequences, vectors based on SV40 or EBV may be used with an appropriate selectable marker.

In bacterial systems, a number of expression vectors may be selected depending upon the use intended for HPK. For example, when large quantities of HPK are needed for the induction of antibodies, vectors which direct high level expression of fusion proteins that are readily purified may be desirable. Such vectors include, but are not limited to, the multifunctional *E. coli* cloning and expression vectors such as BLUESCRIPT® (Stratagene), in which the HPK encoding sequences may be ligated into the vector in frame with sequences for the amino-terminal Met and the subsequent 7 residues of β-galactosidase so that a hybrid protein is produced; pIN vectors (Van Heeke & Schuster (1989) J Biol Chem 264:5503–5509); and the like. pGEX vectors (Promega, Madison Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin or factor XA protease cleavage sites so that the cloned polypeptide of interest can be released from the GST moiety at will.

In the yeast, *Saccharomyces cerevisiae*, a number of vectors containing constitutive or inducible promoters such as alpha factor, alcohol oxidase and PGH may be used. General methodology may be found in Ausubel et al (supra) and Grant et al (1987) Methods in Enzymology 153:516–544.

In cases where plant expression vectors are used, the expression of a sequence encoding HPK may be driven by any of a number of promoters. For example, viral promoters such as the 35S and 19S promoters of CaMV (Brisson et al (1984) Nature 310:511–514) may be used alone or in combination with the omega leader sequence from TMV (Takamatsu et al (1987) EMBO J 6:307–311). Alternatively, plant promoters such as the small subunit of RUBISCO (Coruzzi et al (1984) EMBO J 3:1671–1680; Broglie et al (1984) Science 224:838–843); or heat shock promoters (Winter J and Sinibaldi R M (1991) Results Probl Cell Differ 17:85–105) may be used. These constructs can be introduced into plant cells by direct DNA transformation or pathogen-mediated transfection. For reviews of such techniques, see Hobbs S or Murry L E in McGraw Hill *Yearbook of Science and Technology* (1992) McGraw Hill New York N.Y., pp 191–196 or Weissbach and Weissbach (1988) *Methods for Plant Molecular Biology*, Academic Press, New York N.Y., pp 421–463.

An alternative expression system which could be used to express HPK encoding sequences is an insect system. In one such system, *Autographa californica* nuclear polyhedrosis virus (AcNPV) is used as a vector to express foreign genes in *Spodoptera frugiperda* cells or in Trichonlusia larvae. The HPK encoding sequences may be cloned into a nonessential region of the virus, such as the polyhedrin gene, and placed under control of the polyhedrin promoter. Successful insertion of HPK encoding sequences will render the polyhedrin gene inactive and produce recombinant virus lacking coat protein coat. The recombinant viruses may then be used to infect *S. frugiperda* cells or Trichonlusia larvae in which HPK is expressed (Smith et al (1983) J Virol 46:584; Engelhard E K et al (1994) Proc Nat Acad Sci 91:3224–7).

In mammalian host cells, a number of viral-based expression systems may be utilized. In cases where an adenovirus is used as an expression vector, an HPK encoding sequence may be ligated into an adenovirus transcription/translation complex consisting of the late promoter and tripartite leader sequence. Insertion in a nonessential E1 or E3 region of the viral genome will result in a viable virus capable of expressing HPK in infected host cells (Logan and Shenk (1984) Proc Natl Acad Sci 81:3655–59). In addition, transcription enhancers, such as the rous sarcoma virus (RSV) enhancer, may be used to increase expression in mammalian host cells.

Specific initiation signals may also be required for efficient translation of an HPK encoding sequence. These signals include the ATG initiation codon and adjacent sequences. In cases where an HPK encoding sequence, its initiation codon and upstream sequences are inserted into the appropriate expression vector, no additional translational control signals may be needed. However, in cases where only coding sequence, or a portion thereof, is inserted, exogenous transcriptional control signals including the ATG initiation codon should be provided. Furthermore, the initiation codon must be in the correct reading frame to ensure transcription of the entire insert. Exogenous transcriptional elements and initiation codons can be of various origins, both natural and synthetic. The efficiency of expression may be enhanced by the inclusion of enhancers appropriate to the cell system in use (Scharf D et al (1994) Results Probl Cell Differ 20:125–62; Bittner et al (1987) Methods in Enzymol 153:516–544).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation and acylation. Post-translational processing which cleaves a "prepro" form of the protein may also be important for correct insertion, folding and/or function. Different host cells such as CHO, HeLa, MDCK, 293, WI38, etc have specific cellular machinery and characteristic mechanisms for such post-translational activities and may be chosen to ensure the correct modification and processing of the introduced, foreign protein.

For long-term, high-yield production of recombinant proteins, stable expression is preferred. For example, cell lines which stably express HPK encoding sequences may be transformed using expression vectors which contain viral origins of replication or endogenous expression elements and a selectable marker gene. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clumps of stably transformed cells can be proliferated using tissue culture techniques appropriate to the cell type.

Any number of selection systems may be used to recover transformed cell lines. These include, but are not limited to, the herpes simplex virus thymidine kinase and adenine phosphoribosyltransferase genes which can be employed in tk- or aprt-cells, respectively (Wigler M et al (1977) Cell 11:223–32; Lowy I et al (1980) Cell 22:817–23). Also, antimetabolite, antibiotic or herbicide resistance can be used as the basis for selection; for example, dhfr which confers resistance to methotrexate; npt, which confers resistance to the aminoglycosides neomycin and G-418 and als or pat, which confer resistance to chlorsulfuron and phosphinotricin acetyltransferase, respectively (Wigler M et al (1980) Proc Natl Acad Sci 77:3567–70; Colbere-Garapin F et al (1981) J Mol Biol 150:1–14; Murry, supra). Additional selectable genes may be used, for example, trpB, which allows cells to utilize indole in place of tryptophan, or hisD, which allows cells to utilize histinol in place of histidine (Hartman S C and R C Mulligan (1988) Proc Natl Acad Sci 85:8047–51). Visible markers such as anthocyanins, βglucuronidase and its substrate, GUS, and luciferase and its substrate, luciferin, may be used not only to identify transformants, but also to quantify the amount of transient or stable protein expression attributable to a specific vector system (Rhodes C A et al (1995) Methods Mol Biol 55:121–131).

Identification of Transformants Containing the Polynucleotide Sequence

Although the presence/absence of marker gene expression suggests that the gene of interest is also present, its presence and expression should be confirmed. For example, if the HPK encoding sequence is inserted within a marker gene sequence, recombinant cells containing HPK encoding sequences can be identified by the absence of marker gene function. Alternatively, a marker gene can be placed in tandem with an HPK sequence under the control of a single promoter. Expression of the marker gene in response to induction or selection usually indicates expression of the tandem HPK encoding sequence as well.

Alternatively, host cells which contain the HPK encoding sequence and express HPK may be identified by a variety of procedures known to those of skill in the art. These procedures include, but are not limited to, DNA—DNA or DNA-RNA hybridization and protein bioassay or immunoassay techniques which include membrane, solution, or chip based technologies for the detection and/or quantification of the nucleic acid or protein.

The presence of the polynucleotide sequence encoding HPK can be detected by DNA—DNA or DNA-RNA hybridization or amplification using probes, portions or fragments of HPK encoding sequences. Nucleic acid amplification based assays involve the use of oligonucleotides or oligomers based on the sequence encoding HPK to detect transformants containing HPK encoding sequences in DNA or RNA. As used herein "oligonucleotides" or "oligomers" refer to a nucleic acid sequence of at least about 10 nucleotides and as many as about 60 nucleotides, preferably about 15 to 30 nucleotides, and more preferably about 20–25 nucleotides which can be used as a probe or amplimer.

A variety of protocols for detecting and measuring the expression of HPK, using either polyclonal or monoclonal antibodies specific for the protein are well known in the art. Examples include enzyme-linked immunosorbent assay (ELISA), radioimmunoassay (RIA) and fluorescent activated cell sorting (FACS). A two-site, monoclonal-based immunoassay utilizing monoclonal antibodies reactive to two non-interfering epitopes on HPK is preferred, but a competitive binding assay may be employed. These and other assays are described, among other places, in Hampton R et al (1990, Serological Methods, a Laboratory Manual, APS Press, St Paul Minn.) and Maddox D E et al (1983, J Exp Med 158:1211).

A wide variety of labels and conjugation techniques are known by those skilled in the art and can be used in various nucleic acid and amino acid assays. Means for producing labeled hybridization or PCR probes for detecting sequences related to HPK encoding sequences include oligolabeling, nick translation, end-labeling or PCR amplification using a labeled nucleotide. Alternatively, the HPK encoding sequence, or any portion of it, may be cloned into a vector for the production of an mRNA probe. Such vectors are known in the art, are commercially available, and may be used to synthesize RNA probes in vitro by addition of an appropriate RNA polymerase such as T7, T3 or SP6 and labeled nucleotides. A number of commercial kits or protocols for these procedures may be obtained from companies such as Pharmacia Biotech (Piscataway N.J.), Promega (Madison Wis.), and US Biochemical Corp (Cleveland Ohio). Suitable reporter molecules or labels include those radionuclides, enzymes, fluorescent, chemiluminescent, or chromogenic agents as well as substrates, cofactors, inhibitors, magnetic particles and the like. Protocols for using these labels are widely available in the art. One may also produce recombinant immunoglobulins by methods provided in the art.

Purification of HPK

Host cells transformed with a nucleotide sequence encoding HPK may be cultured under conditions suitable for the expression and recovery of the encoded protein from cell culture. The protein produced by a recombinant cell may be secreted or contained intracellularly depending on the sequence and/or the vector used. As will be understood by those of skill in the art, expression vectors containing polynucleotides encoding HPK can be designed with signal sequences which direct secretion of HPK through a prokaryotic or eukaryotic cell membrane. Other recombinant constructions may be used to join HPK encoding sequences to a nucleotide sequence encoding a polypeptide domain which will facilitate purification of soluble proteins as described in (Kroll D J et al (1993) DNA Cell Biol 12:441–53).

HPK may also be expressed as a recombinant protein with one or more additional polypeptide domains added to facilitate protein purification. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp, Seattle Wash.). The inclusion of a cleavable linker sequences such as Factor XA or enterokinase (Invitrogen, San Diego Calif.) between the purification domain and HPK is useful to facilitate purification. One such expression vector which provides for expression of a fusion protein comprising an HPK contains nucleic acid encoding 6 histidine residues followed by thioredoxin and an enterokinase cleavage site. The histidine residues facilitate purification on IMIAC (immobilized metal ion affinity chromatography as described in Porath et al (1992) Protein Expression and Purification 3: 263–281) while the enterokinase cleavage site provides a means for purifying the neuronatin from the fusion protein.

In addition to recombinant production, fragments of HPK may be produced by direct peptide synthesis using solid-phase techniques (cf Stewart et al (1969) Solid-Phase Peltide Synthesis, W H Freeman Co, San Francisco; Merrifield J (1963) J Am Chem Soc 85:2149–2154). In vitro protein synthesis may be performed using manual techniques or by automation. Automated synthesis may be achieved, for example, using Applied Biosystems 431A Peptide Synthesizer (Perkin Elmer, Foster City Calif.) in accordance with the instructions provided by the manufacturer. Various fragments of HPK may be chemically synthesized separately and combined using chemical methods to produce the full length molecule.

Therapeutic and Diagnostic Uses of HPK Protein

The rationale for the use of nucleotide and polypeptide sequences disclosed herein is based in part on the chemical and structural homology among the novel HPK and known protein kinases from C. elegans (GI 1082115) rat (GI 294637) and man (GI 1117791) (Wilson et al, supra; Webster et al, supra; Creasy et al, supra). Because of the widespread roles for protein kinases in cell signalling processes in various cells and tissues, altered HPK expression may be implicated in a variety of disorders and diseases.

HPK-1, by virtue of its occurrence in hippocampus, may be involved in memory and learning, and associated with disorders such as Alzheimers disease. Therefore, increasing HPK-1 activity through gene therapy using sequences encoding HPK-1 or by administering agonists of HPK-1 may be useful to reverse memory loss due to Alzheimers.

HPK-2 was identified in lymphocytes and associated with a variety of tumor tissues as well as with rheumatoid arthritis. HPK-2 may function in tumor promotion and may therefore provide a target for suppression by antisense molecules of sequences encoding HPK-2 or antagonists of HPK-2 activity as a cancer treatment strategy. Likewise, HPK-2 activity may promote the inflammatory response in arthritis conditions and again provide a target for suppression by antisense molecules of sequences encoding HPK-2 or antagonists of HPK-2 activity.

HPK-3 is derived from macrophages which suggests possible involvement in immune response or inflamation. The significant homology between HPK-3 and a glucocorticoid-regulated rat protein kinase, GI 294637, suggests that HPK-3 may be similarly regulated. HPK-3 expression may therefore be involved in the anti-inflammatory and immunosuppressive effects of glucocorticoid treatment for such conditions as asthma, multiple sclerosis, rheumatoid arthritis, as well as for certain cancers such as lymphocytic leukemias and lymphomas. Thus, increasing HPK-3 expression through gene therapy or through administration of agonists of HPK-3 may augment or provide an alternative to glucocorticoid treatment for these conditions.

HPK and/or a cell line that expresses HPK may be used to evaluate, screen and identify compounds, synthetic drugs, antibodies, peptides or other molecules that modulate the activity of HPK and may therefore be useful in the treatment of disease conditions associated with expression of HPK.
HPK Antibodies HPK-specific antibodies may be useful for the diagnosis of conditions and diseases associated with expression of HPK. Such antibodies may include, but are not limited to, polyclonal, monoclonal, chimeric, single chain, Fab fragments and fragments produced by a Fab expression library. Neutralizing antibodies,such as, those which inhibit dimer formation, are especially preferred for diagnostics and therapeutics.

For the production of antibodies, various hosts including goats, rabbits, rats, mice, etc may be immunized by injection with HPK or any portion, fragment or oligopeptide which retains immunogenic properties. It is not necessary that the protein fragment or oligopeptide used for antibody induction have a functional biological activity, however,it must be antigenic. Peptides used to induce specific antibodies may have an amino acid sequence consisting of at least five amino acids, preferably at least 10 amino acids. Preferably they should mimic a portion of the amino acid sequence of the natural protein and may contain the entire amino acid sequence of a small, naturally occurring molecule. Short stretches of HPK amino acids may be fused with those of another protein such as keyhole limpet hemocyanin and antibody produced against the chimeric molecule. Procedures well known in the art can be used for the production of antibodies to HPK.

Depending on the host species, various adjuvants may be used to increase immunological response. Such adjuvants include but are not limited to Freund's, mineral gels such as aluminum hydroxide, and surface active substances such as lysolecithin, pluronic polyols, polyanions, peptides, oil emulsions, keyhole limpet hemocyanin, and dinitrophenol. BCG (bacilli Calmette-Guerin) and *Corynebacterium parvum* are potentially useful human adjuvants.

Monoclonal antibodies to HPK may be prepared using any technique which provides for the production of antibody molecules by continuous cell lines in culture. These include but are not limited to the hybridoma technique originally described by Koehler and Milstein (1975 Nature 256:495–497), the human B-cell hybridoma technique (Kosbor et al (1983) Immunol Today 4:72; Cote et al (1983) Proc Natl Acad Sci 80:2026–2030) and the EBV-hybridoma technique (Cole et al (1985) *Monoclonal Antibodies and Cancer Therapy*, Alan R Liss Inc, New York N.Y., pp 77–96).

In addition, techniques developed for the production of "chimeric antibodies", the splicing of mouse antibody genes to human antibody genes to obtain a molecule with appropriate antigen specificity and biological activity can be used (Morrison et al (1984) Proc Natl Acad Sci 81:6851–6855; Neuberger et al (1984) Nature 312:604–608; Takeda et al (1985) Nature 314:452–454). Alternatively, techniques described for the production of single chain antibodies (U.S. Pat. No. 4,946,778) can be adapted to produce HPK-specific single chain antibodies Antibodies may also be produced by inducing in vivo production in the lymphocyte population or by screening recombinant immunoglobulin libraries or panels of highly specific binding reagents as disclosed in Orlandi et al (1989, Proc Natl Acad Sci 86: 3833–3837), and Winter G and Milstein C (1991; Nature 349:293–299).

Antibody fragments which contain specific binding sites for HPK may also be generated. For example, such fragments include, but are not limited to, the F(ab')2 fragments which can be produced by pepsin digestion of the antibody molecule and the Fab fragments which can be generated by reducing the disulfide bridges of the F(ab')2 fragments. Alternatively, Fab expression libraries may be constructed to allow rapid and easy identification of monoclonal Fab fragments with the desired specificity (Huse W D et al. (1989) Science 256:1275–1281).

A variety of protocols for competitive binding or immunoradiometric assays using either polyclonal or monoclonal antibodies with established specificities are well known in the art. Such immunoassays typically involve the formation of complexes between HPK and its specific antibody and the measurement of complex formation. A two-site, monoclonal-based immunoassay utilizing monoclonal antibodies reactive to two non-interfering epitopes on a specific HPK protein is preferred, but a competitive binding assay may also be employed. These assays are described in Maddox D E et al (1983, J Exp Med 158:1211).
Diagnostic Assays Using HPK Specific Antibodies Particular HPK antibodies may be used for the diagnosis of conditions or diseases characterized by expression of HPK or in assays to monitor patients being treated with HPK agonists or antagonists. Diagnostic assays for HPK include methods utilizing the antibody and a label to detect HPK in human body fluids or extracts of cells or tissues. The polypeptides and antibodies of the present invention may be used with or without modification. Frequently, the polypeptides and antibodies will be labeled by joining them, either covalently or noncovalently, with a reporter molecule. A wide variety of reporter molecules are known, several of which are described above.

A variety of protocols for measuring HPK, using either polyclonal or monoclonal antibodies specific for the respective protein are known in the art. Examples include enzyme-linked immunosorbent assay (ELISA), radioimmunoassay (RIA) and fluorescent activated cell sorting (FACS). A two-site, monoclonal-based immunoassay utilizing monoclonal antibodies reactive to two non-interfering epitopes on HPK is preferred, but a competitive binding assay may be employed. These assays are described, among other places, in Maddox, D E et al (1983, J Exp Med 158:1211).

In order to provide a basis for diagnosis, normal or standard values for HPK expression must be established. This is accomplished by combining body fluids or cell extracts taken from normal subjects, either animal or human, with antibody to HPK under conditions suitable for complex formation which are well known in the art. The amount of standard complex formation may be quantified by comparing various artificial membranes containing known quantities of HPK with both control and disease samples from biopsied tissues. Then, standard values obtained from normal samples may be compared with values obtained from samples from subjects symptomatic of the disease. Deviation between standard and subject values establishes the presence of a disease state.
Drug Screening HPK, its catalytic or immunogenic fragments or oligopeptides thereof, can be used for screening therapeutic compounds in any of a variety of drug screening techniques. The fragment employed in such a test may be free in solution, affixed to a solid support, borne on a cell surface, or located intracellularly. The formation of binding complexes, between HPK and the agent being tested, may be measured.

Another technique for drug screening which may be used provides for high throughput screening of compounds having suitable binding affinity to HPK(WO Application 84/03564, incorporated herein by reference). In summary, large numbers of different small peptide test compounds are synthesized on a solid substrate, such as plastic pins or some other surface. The peptide test compounds are reacted with fragments of HPK and washed. Bound HPK is then detected by methods well known in the art. Substantially purified HPK can also be coated directly onto plates for use in the aforementioned drug screening techniques. Alternatively, non-neutralizing antibodies can be used to capture the peptide and immobilize it on a solid support.

This invention also contemplates the use of competitive drug screening assays in which neutralizing antibodies capable of binding HPK specifically compete with a test compound for binding HPK. In this manner, the antibodies can be used to detect the presence of any peptide which shares one or more antigenic determinants with HPK.

Diagnostic and Therapeutic Uses of the Polynucleotide Encoding HPK

A polynucleotide designated herein as an HPK encoding sequence, or any part thereof, may be used for diagnostic and/or therapeutic purposes. For diagnostic purposes, the HPK encoding sequences of this invention may be used to detect and quantitate gene expression in biopsied tissues in which expression of HPK encoding sequences may be implicated. The diagnostic assay is useful to distinguish between absence, presence, and excess expression of HPK encoding sequences and to monitor regulation of HPK encoding sequences levels during therapeutic intervention. The association of HPK with disorders and disease conditions in specific tissues would greatly facilitate studies aimed at determining HPK function in these conditions and the development of therapeutic strategies to treat them. Included in the scope of the invention are oligonucleotide sequences, antisense RNA and DNA molecules, and PNAs.

In another embodiment of the subject invention hybridization or PCR are probes provided which are capable of detecting polynucleotide sequences, including genomic sequences, encoding HPK or closely related molecules. The specificity of the probe, whether it is made from a highly specific region, eg, 10 unique nucleotides in the 5' regulatory region, or a less specific region, eg, especially in the 3' region, and the stringency of the hybridization or amplification (maximal, high, intermediate or low) will determine whether the probe identifies only naturally occurring HPK encoding sequences, alleles or related sequences.

Probes may also be used for the detection of related sequences and should preferably contain at least 50% of the nucleotides from any of these HPK encoding sequences. The hybridization probes of the subject invention may be derived from the nucleotide sequences of SEQ ID Nos:2, 4, and 6 or from genomic sequences including promoter, enhancer elements and introns of the naturally occurring HPK encoding sequences. Hybridization probes may be labeled by a variety of reporter groups, including radionuclides such as $^{32}$P or 35S, or enzymatic labels such as alkaline phosphatase coupled to the probe via avidin/biotin coupling systems, and the like.

Other means for producing specific hybridization probes for HPK encoding sequences DNAs include the cloning of nucleic acid sequences encoding HPK or HPK derivatives into vectors for the production of mRNA probes. Such vectors are known in the art and are commercially available and may be used to synthesize RNA probes in vitro by means of the addition of the appropriate RNA polymerase as T7 or SP6 RNA polymerase and the appropriate radioactively labeled nucleotides.

Polynucleotide sequences encoding HPK may be used for the diagnosis of conditions or diseases with which the expression of HPK is associated. For example, polynucleotide sequences encoding HPK may be used in hybridization or PCR assays of fluids or tissues from biopsies to detect HPK encoding sequences expression. The form of such qualitative or quantitative methods may include southern or northern analysis, dot blot or other membrane-based technologies; PCR technologies; dip stick, pin, chip and ELISA technologies. All of these techniques are well known in the art and are the basis of many commercially available diagnostic kits.

The HPK encoding nucleotide sequences disclosed herein provide the basis for assays that detect activation or induction of HPK encoding sequences associated with specific diseases. The HPK encoding nucleotide sequence may be labeled by methods known in the art and added to a fluid or tissue sample from a patient under conditions suitable for the formation of hybridization complexes. After an incubation period, the sample is washed with a compatible fluid which optionally contains a dye (or other label requiring a developer) if the nucleotide has been labeled with an enzyme. After the compatible fluid is rinsed off, the dye is quantitated and compared with a standard. If the amount of dye in the biopsied or extracted sample is significantly elevated over that of a comparable control sample, the nucleotide sequence has hybridized with nucleotide sequences in the sample, and the presence of elevated levels of HPK encoding nucleotide sequence in the sample indicates the presence of the associated disease.

Such assays may also be used to evaluate the efficacy of a particular therapeutic treatment regime in animal studies, in clinical trials, or in monitoring the treatment of an individual patient. In order to provide a basis for the diagnosis of disease, a normal or standard profile for HPK encoding sequence expression must be established. This is accomplished by combining body fluids or cell extracts taken from normal subjects, either animal or human, with an HPK encoding sequence, or a portion thereof, under conditions suitable for hybridization or amplification. Standard hybridization may be quantified by comparing the values obtained for normal subjects with a dilution series of an HPK encoding sequence run in the same experiment where a known amount of substantially purified HPK encoding sequence is used. Standard values obtained from normal samples may be compared with values obtained from samples from patients afflicted with HPK-associated diseases. Deviation between standard and subject values is used to establish the presence of disease.

Once disease is established, a therapeutic agent is administered and a treatment profile is generated. Such assays may be repeated on a regular basis to evaluate whether the values in the profile progress toward or return to the normal or standard pattern. Successive treatment profiles may be used to show the efficacy of treatment over a period of several days or several months.

PCR may be used to provide additional uses for oligonucleotides based upon the HPK sequence. Such oligomers are generally chemically synthesized, but they may be generated enzymatically or produced from a recombinant source. Oligomers generally comprise two nucleotide sequences, one with sense orientation (5'→3') and one with antisense (3'←5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Additionally, methods which may be used to quantitate the expression of a particular molecule include radiolabeling or biotinylating nucleotides, coamplification of a control nucleic acid, and standard curves onto which the experimental results are interpolated (Melby P C et al (1993) J Immunol Methods 159:235–44; Duplaa C et al (1993) Anal Biochem 229–36). Quantitation of multiple samples may be accelerated by running the assay in an ELISA format where the oligomer of interest is presented in various dilutions and a spectrophotometric or colorimetric response gives rapid quantitation. A definitive diagnosis of this type may allow health professionals to begin aggressive treatment and prevent further degeneration of the condition. Similarly, further assays can be used to monitor the progress of a patient during treatment. Furthermore, the nucleotide sequences disclosed herein may be used in molecular biology techniques that have not yet been developed, provided the new techniques rely on properties of nucleotide sequences that are currently known such as the triplet genetic code, specific base pair interactions, and the like.

For therapeutic purposes, an antisense molecule of an HPK encoding sequence may provide a basis for treatment where down-regulation of the gene and consequent inhibition of its activity is desirable. Alternatively, sequences encoding HPK may provide the basis for gene therapy in conditions where it may be desirable to increase expression of HPK and hence increase its activity.

Expression vectors derived from retroviruses, adenovirus, herpes or vaccinia viruses, or from various bacterial plasmids, may be used for delivery of nucleotide sequences to the targeted organ, tissue or cell population. Methods which are well known to those skilled in the art can be used to construct recombinant vectors which will express antisense HPK. See, for example, the techniques described in Sambrook et al (supra) and Ausubel et al (supra).

The polynucleotides comprising full length cDNA sequences encoding HPK and/or its regulatory elements may be used in research as an investigative tool in sense or antisense regulation of gene function (Youssoufian H and H F Lodish 1993 Mol Cell Biol 13:98–104; Eguchi et al (1991) Annu Rev Biochem 60:631–652). Such technology is now well known in the art, and sense or antisense oligomers, or larger fragments, can be designed from various locations along the coding or control regions.

Genes encoding HPK can be turned off by transfecting a cell or tissue with expression vectors which express high levels of a desired HPK encoding sequence fragment. Such constructs can flood cells with untranslatable sense or antisense sequences. Even in the absence of integration into the DNA, such vectors may continue to transcribe RNA molecules until all copies are disabled by endogenous nucleases. Transient expression may last for a month or more with a non-replicating vector and even longer if appropriate replication elements are part of the vector system (Mettler I, personal communication).

As mentioned above, modifications of gene expression can be obtained by designing antisense molecules, DNA, RNA or PNA, to the control regions of HPK encoding sequences, ie, the promoters, enhancers, and introns. Oligonucleotides derived from the transcription initiation site, eg, between –10 and +10 regions of the leader sequence, are preferred. The antisense molecules may also be designed to block translation of mRNA by preventing the transcript from binding to ribosomes. Similarly, inhibition can be achieved using "triple helix" base-pairing methodology. Triple helix pairing compromises the ability of the double helix to open sufficiently for the binding of polymerases, transcription factors, or regulatory molecules. Recent therapeutic advances using triplex DNA were reviewed by Gee J E et al (In: Huber B E and B I Carr (1994) *Molecular and Immunologic Approaches*, Futura Publishing Co, Mt Kisco N.Y.).

Ribozymes are enzymatic RNA molecules capable of catalyzing the specific cleavage of RNA. The mechanism of ribozyme action involves sequence-specific hybridization of the ribozyme molecule to complementary target RNA, followed by endonucleolytic cleavage. Another embodiment involves engineering hammerhead motif ribozyme molecules that can specifically and efficiently catalyze endonucleolytic cleavage of HPK encoding sequences. Specific ribozyme cleavage sites within any potential RNA target are initially identified by scanning the target molecule for ribozyme cleavage sites which include the following sequences, GUA, GUU and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Antisense molecules and ribozymes of the invention may be prepared by any method known in the art for the synthesis of RNA molecules. These include techniques for chemically synthesizing oligonucleotides such as solid phase phosphoramidite chemical synthesis. Alternatively, RNA molecules may be generated by in vitro and in vivo transcription of DNA sequences encoding HPK. Such DNA sequences may be incorporated into a wide variety of vectors with suitable RNA polymerase promoters such as T7 or SP6. Alternatively, antisense cDNA constructs that synthesize antisense RNA constitutively or inducibly can be introduced into cell lines, cells or tissues.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine and wybutosine as well as acetyl-, methyl-, thio- and similarly modified forms of adenine, cytidine, guanine, thymine, and uridine which are not as easily recognized by endogenous endonucleases.

Methods for introducing vectors into cells or tissues include those methods discussed infra and which are equally suitable for in vivo, in vitro and ex vivo therapy. For ex vivo therapy, vectors may be introduced into stem cells taken from the patient and clonally propagated for autologous transplant back into that same patient. Delivery by transfection and by liposome are quite well known in the art.

Furthermore, the nucleotide sequences for HPK encoding sequences disclosed herein may be used in molecular biology techniques that have not yet been developed, provided the new techniques rely on properties of nucleotide sequences that are currently known, including but not limited to such properties as the triplet genetic code and specific base pair interactions.

Detection and Mapping of Related Polynucleotide Sequences

The nucleic acid sequence for HPK can also be used to generate hybridization probes for mapping the naturally occurring genomic sequence. The sequence may be mapped to a particular chromosome or to a specific region of the chromosome using well known techniques. These include in situ hybridization to chromosomal spreads, flow-sorted chromosomal preparations, or artificial chromosome constructions such as yeast artificial chromosomes, bacterial artificial chromosomes, bacterial P1 constructions or single chromosome cDNA libraries as reviewed in Price C M (1993; Blood Rev 7:127–34) and Trask B J (1991; Trends Genet 7:149–54).

The technique of fluorescent in situ hybridization of chromosome spreads has been described, among other places, in Verma et al (1988) *Human Chromosomes: A Manual of Basic Techniques*, Pergamon Press, New York N.Y. Fluorescent in situ hybridization of chromosomal preparations and other physical chromosome mapping techniques may be correlated with additional genetic map data. Examples of genetic map data can be found in the 1994 Genome Issue of Science (265:1981f). Correlation between the location of an HPK encoding sequence on a physical chromosomal map and a specific disease (or predisposition to a specific disease) may help delimit the region of DNA associated with that genetic disease. The nucleotide sequences of the subject invention may be used to detect differences in gene sequences between normal, carrier or affected individuals.

In situ hybridization of chromosomal preparations and physical mapping techniques such as linkage analysis using established chromosomal markers may be used for extending genetic maps. For example, a sequence tagged site based map of the human genome was recently published by the Whitehead-MIT Center for Genomic Research (Hudson T J et al (1995) Science 270:1945–1954). Often the placement of a gene on the chromosome of another mammalian species such as mouse (Whitehead Institute/MIT Center for Genome Research, Genetic Map of the Mouse, Database Release 10, Apr. 28, 1995) may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once a disease or syndrome, such as ataxia telangiectasia (AT), has been crudely localized by genetic linkage to a particular genomic region, for example, AT to 11q22-23 (Gatti et al (1988) Nature 336:577–580), any sequences mapping to that area may represent associated or regulatory genes for further investigation. The nucleotide sequence of the subject invention may also be used to detect differences in the chromosomal location due to translocation, inversion, etc. among normal, carrier or affected individuals Pharmaceutical Compositions The present invention relates to pharmaceutical compositions which may comprise nucleotides, proteins, antibodies, agonists, antagonists, or inhibitors, alone or in combination with at least one other agent, such as stabilizing compound, which may be administered in any sterile, biocompatible pharmaceutical carrier, including, but not limited to, saline, buffered saline, dextrose, and water. Any of these molecules can be administered to a patient alone, or in combination with other agents, drugs or hormones, in pharmaceutical compositions where it is mixed with excipient(s) or pharmaceutically acceptable carriers. In one embodiment of the present invention, the pharmaceutically acceptable carrier is pharmaceutically inert.

Administration of Pharmaceutical Compositions

Pharmaceutical compositions may be administered to any subject in need of treatment including, but not limited to, humans and domestic animals. Administration of pharmaceutical compositions is accomplished orally or parenterally. Methods of parenteral delivery include topical, intra-arterial (directly to the tumor), intramuscular, subcutaneous, intramedullary, intrathecal, intraventricular, intravenous, intraperitoneal, or intranasal administration. In addition to the active ingredients, these pharmaceutical compositions may contain suitable pharmaceutically acceptable carriers comprising excipients and auxiliaries which facilitate processing of the active compounds into preparations which can be used pharmaceutically. Further details on techniques for formulation and administration may be found in the latest edition of "Remington's Pharmaceutical Sciences" (Maack Publishing Co, Easton Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers such as sugars, including lactose, sucrose, mannitol, or sorbitol; starch from corn, wheat, rice, potato, or other plants; cellulose such as methyl cellulose, hydroxypropylmethylcellulose, or sodium carboxymethylcellulose; and gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, ie, dosage.

Pharmaceutical preparations which can be used orally include push-fit capsules made of gelatin, as well as soft, sealed capsules made of gelatin and a coating such as glycerol or sorbitol. Push-fit capsules can contain active ingredients mixed with a filler or binders such as lactose or starches, lubricants such as talc or magnesium stearate, and, optionally, stabilizers. In soft capsules, the active compounds may be dissolved or suspended in suitable liquids, such as fatty oils, liquid paraffin, or liquid polyethylene glycol with or without stabilizers.

Pharmaceutical formulations for parenteral administration include aqueous solutions of active compounds. For injection, the pharmaceutical compositions of the invention may be formulated in aqueous solutions, preferably in physiologically compatible buffers such as Hanks's solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

Manufacture and Storage

The pharmaceutical compositions of the present invention may be manufactured in a manner known in the art, eg, by means of conventional mixing, dissolving, granulating, dragee-making, levigating, emulsifying, encapsulating, entrapping or lyophilizing processes.

The pharmaceutical composition may be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preferred preparation may be a lyophilized powder in 1 mM–50 mM histidine, 0.1%–2% sucrose, 2%–7% mannitol at a pH range of 4.5 to 5.5 that is combined with buffer prior to use.

After pharmaceutical compositions comprising a compound of the invention formulated in a acceptable carrier have been prepared, they can be placed in an appropriate container and labeled for treatment of an indicated condition. For administration of HPK, such labeling would include amount, frequency and method of administration.

Therapeutically Effective Dose

Pharmaceutical compositions suitable for use in the present invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, eg, of neoplastic cells, or in animal models, usually mice, rabbits, dogs, or pigs. The animal model is also used to achieve a desirable concentration range and route of administration. Such information can then be used to determine useful doses and routes for administration in humans.

A therapeutically effective dose refers to that amount of protein or its antibodies, antagonists, or inhibitors which ameliorate the symptoms or condition. Therapeutic efficacy and toxicity of such compounds can be determined by standard pharmaceutical procedures in cell cultures or experimental animals, eg, ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50. Pharmaceutical compositions which exhibit large therapeutic indices are preferred. The data obtained from cell culture assays and animal studies is used in formulating a range of dosage for human use. The dosage of such compounds lies preferably within a range of circulating concentrations that include the ED50 with little or no toxicity. The dosage varies within this range depending upon the dosage form employed, sensitivity of the patient, and the route of administration.

The exact dosage is chosen by the individual physician in view of the patient to be treated. Dosage and administration are adjusted to provide sufficient levels of the active moiety or to maintain the desired effect. Additional factors which may be taken into account include the severity of the disease state, eg, tumor size and location; age, weight and gender of the patient; diet, time and frequency of administration, drug combination(s), reaction sensitivities, and tolerance/response to therapy. Long acting pharmaceutical compositions might be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery generally available in the scientific literature. Those skilled in the art will employ different formulations for nucleotides than for proteins or their inhibitors. Similarly, delivery of polynucleotides or polypeptides will be specific to particular cells, conditions, locations, etc.

It is contemplated, for example, that molecules or compounds that modulate HPK activity, such as antibodies of HPK, or an HPK derivative can be delivered in a suitable formulation as a therapeutic agent. Similarly, administration of agonists should also improve the activity or lifespan of this protein and lessen the onset and progression of senescence.

The examples below are provided to illustrate the subject invention and are not included for the purpose of limiting the invention.

EXAMPLES

I HPK-1 HIPONOTO1 cDNA Library Construction

The hippocampus used for this library was obtained from the Keystone Skin Bank, International Institute for the Advancement of Medicine (Exton, Pa.). Hippocampus tissue from 72 year old Caucasian female (RF94-09083) was flash frozen, ground in a mortar and pestle, and lyzed immediately in buffer containing guanidinium isothiocyanate. Lysis was followed by several phenol chloroform extractions and ethanol precipitation. Poly A+ RNA was isolated using biotinylated oligo d(T) primer and streptavidin coupled to paramagnetic particles (Promega Corp, Madison Wis.) and sent to Stratagene. Stratagene prepared the cDNA library using oligo d(T) priming. Synthetic adapter oligonucleotides were ligated onto the cDNA molecules enabling them to be inserted into the UNI-ZAP™ vector system (Stratagene). The quality of the cDNA library was screened using DNA probes, and then the BLUESCRIPT® phagemid (Stratagene) was excised. Subsequently, the custom-constructed library phage particles were infected into *E. coli* host strain XL1 Blue (Stratagene). Alternative unidirectional vectors might include, but are not limited to, pcDNAI (Invitrogen) and pSHlox-1 (Novagen).

The phagemid forms of individual cDNA clones were obtained by the in vivo excision process, in which the host bacterial strain was co-infected with both the library phage and an f1 helper phage. Polypeptides or enzymes derived from both the library-containing phage and the helper phage nicked the DNA, initiated new DNA synthesis from defined sequences on the target DNA, and created a smaller, single stranded circular phagemid DNA molecule that included all DNA sequences of the BLUESCRIPT® phagemid and the cDNA insert. The phagemid DNA was released from the cells and purified, and used to reinfect fresh host cells (SOLR, Stratagene) where double-stranded phagemid DNA was produced. Because the phagemid carries the gene for b-lactamase, the newly transformed bacteria were selected on medium containing ampicillin.

Phagemid DNA was purified using the QIAWELL-8 Plasmid Purification System from the QIAGEN DNA Purification System (QIAGEN Inc, Chatsworth, Calif.). The DNA was eluted from the purification resin and prepared for DNA sequencing and other analytical manipulations.

II HPK-2 TMLR30T01 cDNA Library Construction

The normal peripheral blood T-lymphocytes used for this library were obtained from two 24 year old, Caucasian males. This library represents a mixture of allogeneically stimulated human T cell populations obtained from Ficoll/Hypaque purified buffy coats. The cells from the two different donors (not typed for HLA alleles) were incubated at a density of 1×106/ml, cultured for 96 hours in DME containing 10% human serum, washed in PBS, scraped and lyzed immediately in buffer containing guanidinium isothiocyanate. The lysate was extracted twice with a mixture of phenol and chloroform, pH 8.0 and centrifuged over a CsCl cushion using a Beckman SW28 rotor in a L8-70M Ultracentrifuge (Beckman Instruments). The RNA was precipitated using 0.3M sodium acetate and 2.5 volumes of ethanol, resuspended in water and DNase treated for 15 min at 37° C. The total RNA was isolated using the Qiagen Oligotex kit (QIAGEN Inc, Chatsworth Calif.). It must be noted that B lymphocytes were not removed, and some contaminating macrophages may also have been present. Stratagene (La Jolla Calif.) used the total RNA to construct a custom cDNA library essentially as described above. The cDNAs were inserted into the LAMBDAZAP™ vector system (Stratagene); and the vector was transformed into cells of *E. coli*, strain XL1-BlueMRF (Stratagene). The phagemid forms of individual cDNA clones were obtained by the in vivo excision process previously described.

Plasmid DNA was released from the cells and purified using the Miniprep Kit (Catalogue # 77468; Advanced Genetic Technologies Corporation, Gaithersburg Md.), as previously described (Section V). Alternative methods of purifying plasmid DNA include the use of MAGIC MINIPREPS-DNA Purification System (Catalogue #A7100, Promega, Madison Wis.)or QIAwell-8 Plasmid, QIAwell PLUS DNA and QIAwell ULTRA DNA Purification Systems (QIAGEN Chatsworth Calif.).

III HPK-3 MPHGNOTO3 cDNA Library Construction

Peripheral blood was obtained from a 24 year old, Caucasian male. Mononuclear cells were separated from heparinized venous blood after centrifugation through Ficoll/Hypaque using HISTOPAQUE®-1119 and HISTOPAQUE®-1077, available from Sigma Diagnostics (St Louis Mo.). The Ficoll/Hypaque buffy coat which contains peripheral blood mononuclear cells was put into sterile Petri dishes and cultured for between 3 to 5 days in Dulbecco's minimum essential medium (DME) supplemented with 10% human serum. After incubation, macrophages mostly adhered to the plastic surface, whereas most other cell types, B and T lymphocytes, remained in solution. The DME was decanted from the wells and washed with phosphate buffered saline (PBS). Macrophages were released from the plastic surface by gently scraping the Petri dishes in PBS/1 mM EDTA. Macrophages were lysed immediately in buffer containing guanidinium isothiocyanate.

The lysate was extracted twice with a mixture of phenol and chloroform, pH 8.0 and centrifuged over a CsCl cushion using a Beckman SW28 rotor in a L8-70M Ultracentrifuge (Beckman Instruments). The RNA was precipitated using 0.3M sodium acetate and 2.5 volumes of ethanol, resuspended in water and DNase treated for 15 min at 37%C. The total RNA was isolated using the Qiagen Oligotex kit (QIAGEN Inc, Chatsworth Calif.). It must be noted that some contaminating T and B lymphocytes may also have been present.

The poly A+ RNA was used to construct the MPHGNOTO3 cDNA library, phagemid forms of individual cDNA clones were obtained by the in vivo excision process, and plasmid DNA was released and recovered from the cells using the Miniprep Kit (Catalogue # 77468, Advanced Genetic Technologies Corporation, Gaithersburg Md.), as described above.

IV Sequencing of cDNA Clones

The cDNAs were sequenced by the method of Sanger F and A R Coulson (1975; J Mol Biol 94:441f), using a Catalyst 800 Hamilton Micro Lab 2200 (Hamilton, Reno Nev.) in combination with four Peltier Thermal Cyclers (PTC200 from M J Research, Watertown Mass.) and Applied Biosystems 377 or 373 DNA Sequencing Systems (Perkin Elmer) and the reading frame was determined.

V Homology Searching of cDNA Clones and Their Deduced Proteins

Each cDNA was compared to sequences in GenBank using a search algorithm developed by Applied Biosystems and incorporated into the INHERIT™ 670 Sequence Analysis System. In this algorithm, Pattern Specification Language (TRW Inc, Los Angeles Calif.) was used to determine regions of homology. The three parameters that determine how the sequence comparisons run were window size, window offset, and error tolerance. Using a combination of these three parameters, the DNA database was searched for sequences containing regions of homology to the query sequence, and the appropriate sequences were scored with an initial value. Subsequently, these homologous regions were examined using dot matrix homology plots to distinguish regions of homology from chance matches. Smith-Waterman alignments were used to display the results of the homology search.

Peptide and protein sequence homologies were ascertained using the INHERIT™ 670 Sequence Analysis System in a way similar to that used in DNA sequence homologies. Pattern Specification Language and parameter windows were used to search protein databases for sequences containing regions of homology which were scored with an initial value. Dot-matrix homology plots were examined to distinguish regions of significant homology from chance matches.

BLAST, which stands for Basic Local Alignment Search Tool (Altschul S F (1993) J Mol Evol 36:290–300; Altschul, S F et al (1990) J Mol Biol 215:403–10), was used to search for local sequence alignments. BLAST produces alignments of both nucleotide and amino acid sequences to determine sequence similarity. Because of the local nature of the alignments, BLAST is especially useful in determining exact matches or in identifying homologs. BLAST is useful for matches which do not contain gaps. The fundamental unit of BLAST algorithm output is the High-scoring Segment Pair (HSP).

An HSP consists of two sequence fragments of arbitrary but equal lengths whose alignment is locally maximal and for which the alignment score meets or exceeds a threshold or cutoff score set by the user. The BLAST approach is to look for HSPs between a query sequence and a database sequence, to evaluate the statistical significance of any matches found, and to report only those matches which satisfy the user-selected threshold of significance. The parameter E establishes the statistically significant threshold for reporting database sequence matches. E is interpreted as the upper bound of the expected frequency of chance occurrence of an HSP (or set of HSPs) within the context of the entire database search. Any database sequence whose match satisfies E is reported in the program output.

VI Northern Analysis

Northern analysis is a laboratory technique used to detect the presence of a transcript of a gene and involves the hybridization of a labelled nucleotide sequence to a membrane on which RNAs from a particular cell type or tissue have been bound (Sambrook et al supra). Analogous computer techniques using BLAST (Altschul S F 1993 and 1990, supra) are used to search for identical or related molecules in nucleotide databases such as GenBank or the LIFESEQ® database (Incyte, Palo Alto Calif.). This analysis is much faster than multiple, membrane-based hybridizations. In addition, the sensitivity of the computer search can be modified to determine whether any particular match is categorized as exact or homologous.

The basis of the search is the product score which is defined as:

% sequence identity×% maximum BLAST score/100 and it takes into account both the degree of similarity between two sequences and the length of the sequence match. For example, with a product score of 40, the match will be exact within a 1–2% error; and at 70, the match will be exact. Homologous molecules are usually identified by selecting those which show product scores between 15 and 40, although lower scores may identify related molecules.

VII Extension of HPK to Full Length or to Recover Regulatory Elements

The nucleic acid sequence of full length HPK encoding sequences (SEQ ID Nos:2, 4, or 6) is used to design oligonucleotide primers for extending a partial nucleotide sequence to full length or for obtaining 5' sequences from genomic libraries. One primer is synthesized to initiate extension in the antisense direction (XLR) and the other is synthesized to extend sequence in the sense direction (XLF).

Primers allow the extension of the known HPK encoding sequences "outward" generating amplicons containing new, unknown nucleotide sequences for the region of interest (U.S. patent application Ser. No. 08/487,112). The initial primers are designed from the cDNA using OLIGO® 4.06 Primer Analysis Software (National Biosciences), or another appropriate program, to be 22–30 nucleotides in length, to have a GC content of 50% or more, and to anneal to the target sequence at temperatures about 68%–72% C. Any stretch of nucleotides which would result in hairpin structures and primer—primer dimerizations is avoided.

The original, selected cDNA libraries, or a human genomic library are used to extend the sequence; the latter is most useful to obtain 5' upstream regions. If more extension is necessary or desired, additional sets of primers are designed to further extend the known region.

By following the instructions for the XL-PCR kit (Perkin Elmer) and thoroughly mixing the enzyme and reaction mix, high fidelity amplification is obtained. Beginning with 40 pmol of each primer and the recommended concentrations of all other components of the kit, PCR is performed using the Peltier Thermal Cycler (PTC200; M J Research, Watertown Mass.) and the following parameters:

| | |
|---|---|
| Step 1 | 94% C for 1 min (initial denaturation) |
| Step 2 | 65% C for 1 min |
| Step 3 | 68% C for 6 min |
| Step 4 | 94% C for 15 sec |
| Step 5 | 65% C for 1 min |
| Step 6 | 68% C for 7 min |
| Step 7 | Repeat step. 4–6 for 15 additional cycles |
| Step 8 | 94% C for 15 sec |
| Step 9 | 65% C for 1 min |
| Step 10 | 68% C for 7:15 min |
| Step 11 | Repeat step 8–10 for 12 cycles |

-continued

| | |
|---|---|
| Step 12 | 72% C for 8 min |
| Step 13 | 4% C (and holding) |

A 5–10 liter micro aliquot of the reaction mixture is analyzed by electrophoresis on a low concentration (about 0.6–0.8%) agarose mini-gel to determine which reactions were successful in extending the sequence. Bands thought to contain the largest products were selected and cut out of the gel. Further purification involves using a commercial gel extraction method such as QIAQUICK™ (QIAGEN Inc). After recovery of the DNA, Klenow enzyme was used to trim single-stranded, nucleotide overhangs creating blunt ends which facilitate religation and cloning.

After ethanol precipitation, the products are redissolved in 13 microliter of ligation buffer, 1 microliter T4-DNA ligase (15 units) and 1 microliter T4 polynucleotide kinase are added, and the mixture is incubated at room temperature for 2–3 hours or overnight at 16% C. Competent E. coli cells (in 40 &l of appropriate media) are transformed with 3 microliter of ligation mixture and cultured in 80 &l of SOC medium (Sambrook J et al, supra). After incubation for one hour at 37% C., the whole transformation mixture is plated on Luria Bertani (LB)-agar (Sambrook J et al, supra) containing 2×Carb. The following day, several colonies are randomly picked from each plate and cultured in 150 microliter of liquid LB/2×Carb medium placed in an individual well of an appropriate, commercially-available, sterile 96-well microtiter plate. The following day, 5 microliter of each overnight culture is transferred into a non-sterile 96-well plate and after dilution 1:10 with water, 5 microliter of each sample is transferred into a PCR array.

For PCR amplification, 18 microliter of concentrated PCR reaction mix (3.3×) containing 4 units of rTth DNA polymerase, a vector primer and one or both of the gene specific primers used for the extension reaction are added to each well. Amplification is performed using the following conditions:

| | |
|---|---|
| Step 1 | 94% C for 60 sec |
| Step 2 | 94% C for 20 sec |
| Step 3 | 55% C for 30 sec |
| Step 4 | 72% C for 90 sec |
| Step 5 | Repeat steps 2–4 for an additional 29 cycles |
| Step 6 | 72% C for 180 sec |
| Step 7 | 4% C (and holding) |

Aliquots of the PCR reactions are run on agarose gels together with molecular weight markers. The sizes of the PCR products are compared to the original partial cDNAs, and appropriate clones are selected, ligated into plasmid and sequenced.

VIII Labeling and Use of Hybridization Probes

Hybridization probes derived from SEQ ID NO:2 are employed to screen cDNAs, genomic DNAs or mRNAs. Although the labeling of oligonucleotides, consisting of about 20 base-pairs, is specifically described, essentially the same procedure is used with larger cDNA fragments. Oligonucleotides are designed using state-of-the-art software such as OLIGO 4.06 (National Biosciences), labeled by combining 50 pmol of each oligomer and 250 mCi of [$-^{32}$P] adenosine triphosphate (Amersham, Chicago Ill.) and T4 polynucleotide kinase (DuPont NEN®, Boston Mass.). The labeled oligonucleotides are substantially purified with Sephadex G-25 super fine resin column (Pharmacia). A portion containing $10^7$ counts per minute of each of the sense and antisense oligonucleotides is used in a typical membrane based hybridization analysis of human genomic DNA digested with one of the following endonucleases (Ase I, Bgl II, Eco RI, Pst I, Xba 1, or Pvu II; DuPont NEN®).

The DNA from each digest is fractionated on a 0.7 percent agarose gel and transferred to nylon membranes (Nytran Plus, Schleicher & Schuell, Durham NH). Hybridization is carried out for 16 hours at 40% C. To remove nonspecific signals, blots are sequentially washed at room temperature under increasingly stringent conditions up to 0.1×saline sodium citrate and 0.5% sodium dodecyl sulfate. After XOMAT AR™ film (Kodak, Rochester N.Y.) is exposed to the blots in a Phosphoimager cassette (Molecular Dynamics, Sunnyvale Calif.) for several hours, hybridization patterns are compared visually.

IX Antisense Molecules

The HPK encoding sequence, or any part thereof, is used to inhibit in vivo or in vitro expression of naturally occurring HPK encoding sequences. Although use of antisense oligonucleotides, comprising about 20 base-pairs, is specifically described, essentially the same procedure is used with larger cDNA fragments. For example, an oligonucleotide based on the coding sequence of HPK-1 as shown in FIGS. 1A, 1, 1C, and 1D is used to inhibit expression of naturally occurring HPK. The complementary oligonucleotide is designed from the most unique 5' sequence as shown in FIGS. 1A, 1, 1C, and 1D and used to inhibit translation of an HPK encoding sequences transcript by preventing the ribosome from binding. Using an appropriate portion of the leader and 5' sequence of SEQ ID NO:2, an effective antisense oligonucleotide includes any 15–20 nucleotides spanning the region which translates into the signal or early coding sequence of the polypeptide as shown in FIG. 1A, 1, 1C, and 1D.

X Expression of HPK

Expression of the HPK is accomplished by subcloning the cDNAs into appropriate vectors and transfecting the vectors into host cells. In this case, the cloning vector, PSPORT™, previously used for the generation of the cDNA library is used to express HPK in E. coli. Upstream of the cloning site, this vector contains a promoter for β-galactosidase, followed by sequence containing the amino-terminal Met and the subsequent 7 residues of β-galactosidase. Immediately following these eight residues is a bacteriophage promoter useful for transcription and a linker containing a number of unique restriction sites.

Induction of an isolated, transfected bacterial strain with IPTG using standard methods produces a fusion protein which consists of the first seven residues of β-galactosidase, about 5 to 15 residues of linker, and the full length HPK. The signal sequence directs the secretion of HPK into the bacterial growth media which can be used directly in the following assay for activity.

XI HPK Activity

HPK activity may be measured by phosphorylation of a protein substrate using gamma-labeled $^{32}$P-ATP and quantitation of the incorporated radioactivity using a gamma radioisotope counter. HPK is incubated with the protein substrate, $^{32}$P-ATP, and a kinase buffer. The 32P incorporated into the substrate is then separated from free $^{32}$P-ATP by electrophoresis and the incorporated 32P is counted. A determination of the specific amino acid residues phosphorylated is made by phosphoamino acid analysis of the hydrolyzed protein as described by Boyle W J et al (1991) Methods in Enzymol 201: 110–148.

XII Production of HPK Specific Antibodies

HPK substantially purified using PAGE electrophoresis (Sambrook, supra) is used to immunize rabbits and to produce antibodies using standard protocols. The amino acid sequence translated from HPK is analyzed using DNASTAR™ software (DNASTAR Inc) to determine regions of high immunogenicity and a corresponding oligopolypeptide is synthesized and used to raise antibodies by means known to those of skill in the art. Analysis to select appropriate epitopes, such as those near the C-terminus or in hydrophilic regions is described by Ausubel F M et al (supra).

Typically, the oligopeptides are 15 residues in length, synthesized using an Applied Biosystems Peptide Synthesizer Model 431A using fmoc-chemistry, and coupled to keyhole limpet hemocyanin (KLH, Sigma) by reaction with M-maleimidobenzoyl-N-hydroxysuccinimide ester (MBS; Ausubel F M et al, supra). Rabbits are immunized with the oligopeptide-KLH complex in complete Freund's adjuvant. The resulting antisera are tested for antipeptide activity, for example, by binding the peptide to plastic, blocking with 1% BSA, reacting with rabbit antisera, washing, and reacting with radioiodinated, goat anti-rabbit IgG.

XIII Purification of Naturally Occurring HPK Using Specific Antibodies

Naturally occurring or recombinant HPK is substantially purified by immunoaffinity chromatography using antibodies specific for HPK. An immunoaffinity column is constructed by covalently coupling HPK antibody to an activated chromatographic resin such as CnBr-activated Sepharose (Pharmacia Biotech). After the coupling, the resin is blocked and washed according to the manufacturer's instructions.

Media containing HPK is passed over the immunoaffinity column, and the column is washed under conditions that allow the preferential absorbance of HPK (eg, high ionic strength buffers in the presence of detergent). The column is eluted under conditions that disrupt antibody/HPK binding (eg, a buffer of pH 2–3 or a high concentration of a chaotrope such as urea or thiocyanate ion), and HPK is collected.

XIV Identification of Molecules Which Interact with HPK

HPK, or biologically active fragments thereof, are labelled with $^{125}$I Bolton-Hunter reagent (Bolton A E and Hunter W M (1973) Biochem J 133: 529). Candidate molecules previously arrayed in the wells of a 96 well plate are incubated with the labelled HPK, washed and any wells with labelled HPK complex are assayed. Data obtained using different concentrations of HPK are used to calculate values for the number, affinity, and association of HPK with the candidate molecules.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 233 amino acids
        ( B ) TYPE: amino acid
        ( C ) STRANDEDNESS: single
        ( D ) TOPOLOGY: linear ( i i ) MOLECULE TYPE: peptide ( v i i ) IMMEDIATE SOURCE:
        ( A ) LIBRARY:
        ( B ) CLONE: Consensus ( x i ) SEQUENCE DESCRIPTION: SEQ ID NO:1:

```
Met Met Asp Ala Lys Ala Lys Gln Asp Cys Val Lys Glu Ile Gly Leu
 1               5                  10                  15
Leu Lys Gln Leu Asn His Pro Asn Ile Ile Lys Tyr Leu Asp Ser Phe
            20                  25                  30
Ile Glu Asp Asn Glu Leu Asn Ile Val Leu Glu Leu Ala Asp Ala Gly
        35                  40                  45
Asp Leu Pro Gln Met Ile Lys Tyr Phe Lys Lys Gln Lys Arg Leu Ile
    50                  55                  60
Pro Glu Arg Thr Val Trp Lys Tyr Phe Val Gln Leu Cys Ser Ala Val
65                  70                  75                  80
Glu His Met His Ser Arg Arg Val Met His Arg Asp Ile Lys Pro Ala
                85                  90                  95
Asn Val Phe Ile Thr Ala Thr Gly Val Val Lys Leu Gly Asp Leu Gly
            100                 105                 110
Leu Gly Arg Phe Phe Ser Ser Glu Thr Thr Ala Ala His Ser Leu Val
        115                 120                 125
Gly Thr Pro Tyr Tyr Met Ser Pro Glu Arg Ile His Glu Asn Gly Tyr
    130                 135                 140
Asn Phe Lys Ser Asp Ile Trp Ser Leu Gly Cys Leu Leu Tyr Glu Met
145                 150                 155                 160
Ala Ala Leu Gln Ser Pro Phe Tyr Gly Asp Lys Met Asn Leu Phe Ser
                165                 170                 175
Leu Cys Gln Lys Ile Glu Gln Cys Asp Tyr Pro Pro Leu Pro Gly Glu
            180                 185                 190
His Tyr Ser Glu Lys Leu Arg Glu Leu Val Ser Met Cys Ile Cys Pro
        195                 200                 205
Asp Pro His Gln Arg Pro Asp Ile Gly Xaa Val His Gln Val Ala Lys
    210                 215                 220
Gln Met His Ile Trp Met Ser Ser Xaa
225                 230
```

( 2 ) INFORMATION FOR SEQ ID NO:2:

( i ) SEQUENCE CHARACTERISTICS:
        ( A ) LENGTH: 1347 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
    ( A ) LIBRARY:
    ( B ) CLONE: Consensus ( x i ) SEQUENCE DESCRIPTION: SEQ ID NO:2:

| | | | | | | |
|---|---|---|---|---|---|---|
| CATTCTGGGA | CCTGTTCGCA | GGACCGTCCG | GTGTTCTGGC | CCCCTGATGT | CACCTTCACG | 60 |
| GGCCTGACTC | ACAGTCCTAA | ATATCTGACA | GCGAAGATCG | CTTGTAGTTC | GTGCCCTCGT | 120 |
| GAGGCTGGCA | TGCAGGATGG | CAGGACAGCC | CGGCCACATG | CCCCATGGAG | GGAGTTCCAA | 180 |
| CAACCTCTGC | CACACCCTGG | GGCCTGTGCA | TCCTCCTGAC | CCACAGAGGC | ATCCCAACAC | 240 |
| GCTGTCTTTT | CGCTGCTCGC | TGGCGGACTT | CCAGATCGAA | AAGAAGATAG | GCCGAGGACA | 300 |
| GTTCAGCGAG | GTGTACAAGG | CCACCTGCCT | GCTGGACAGG | AAGACAGTGG | CTCTGRAGAA | 360 |
| GGTGCAGATC | TTTGAGATGA | TGGACGCCAA | GGCGAAGCAG | GACTGTGTCA | AGGAGATCGG | 420 |
| CCTCTTGAAG | CAACTGAACC | ACCCAAATAT | CATCAAGTAT | TTGGACTCCT | TTATCGAAGA | 480 |
| CAACGAACTG | AACATTGTGC | TGGAATTGGC | TGACGCAGGG | GACCTCCCGC | AGATGATCAA | 540 |
| GTACTTTAAG | AAGCAGAAGC | GGCTCATCCC | GGAGAGGACA | GTATGGAAGT | ACTTTGTGCA | 600 |
| GCTGTGCAGC | GCCGTGGAGC | ACATGCATTC | ACGCCGGGTG | ATGCACCGAG | ACATCAAGCC | 660 |
| TGCCAACGTG | TTCATCACAG | CCACGGGCGT | CGTGAAGCTC | GGTGACCTTG | GTCTGGGCCG | 720 |
| CTTCTTCAGC | TCTGAAACCA | CCGCAGCCCA | CTCCCTAGTG | GGGACGCCCT | ACTACATGTC | 780 |
| ACCGGAGAGG | ATCCATGAGA | ACGGCTACAA | CTTCAAGTCC | GACATCTGGT | CCTTGGGCTG | 840 |
| TCTGCTGTAC | GAGATGGCAG | CCCTCCAGAG | CCCCTTCTAT | GGAGATAAGA | TGAATCTCTT | 900 |
| CTCCCTGTGC | CAGAAGATCG | AGCAGTGTGA | CTACCCCCA | CTCCCGGGG | AGCACTACTC | 960 |
| CGAGAAGTTA | CGAGAACTGG | TCAGCATGTG | CATCTGCCCT | GACCCCCACC | AGAGACCTGA | 1020 |
| CATCGGATAM | GTGCACCAGG | TGGCCAAGCA | GATGCACATC | TGGATGTCCA | GCAMCTGAGC | 1080 |
| GTGGATGCAC | CGTGCCTTAT | CAAAGCCAGC | ACCACTTTGC | CTTACTTGAG | TCGTCTTCTC | 1140 |
| TTCGAGTGGC | CACCTGGTAG | CCTAGAACAG | CTAAGACCAC | ANGNTTCAGC | AGGTTCCCCA | 1200 |
| AAAGACTGCC | CAGCCTTACA | GCAGATGCTA | AAGGNAGAGC | AGCTGAGNGA | GGGGCNCTNN | 1260 |
| CCACATNTCA | CTGATGGTCA | GATTCCAAAN | TCCTTTCTTT | ATACTGTTGT | GGACAATCTC | 1320 |
| AGCTGGGTCA | ATAAGGGCAG | TTGGTTC | | | | 1347 |

( 2 ) INFORMATION FOR SEQ ID NO:3:

( i ) SEQUENCE CHARACTERISTICS:
    ( A ) LENGTH: 403 amino acids
    ( B ) TYPE: amino acid
    ( C ) STRANDEDNESS: single
    ( D ) TOPOLOGY: linear ( i i ) MOLECULE TYPE: peptide ( v i i ) IMMEDIATE SOURCE:
    ( A ) LIBRARY:
    ( B ) CLONE: Consensus ( x i ) SEQUENCE DESCRIPTION: SEQ ID NO:3:

| Met | Ala | His | Leu | Arg | Gly | Phe | Ala | Asn | Gln | His | Ser | Arg | Val | Asp | Pro |
|---|---|---|---|---|---|---|---|---|---|---|---|---|---|---|---|
| 1 | | | | 5 | | | | | 10 | | | | | 15 | |

| Glu | Glu | Leu | Phe | Thr | Lys | Leu | Asp | Arg | Ile | Gly | Lys | Gly | Ser | Phe | Gly |
|---|---|---|---|---|---|---|---|---|---|---|---|---|---|---|---|
| | | | 20 | | | | | 25 | | | | | 30 | | |

| Glu | Val | Tyr | Lys | Gly | Ile | Asp | Asn | His | Thr | Lys | Glu | Val | Val | Ala | Ile |
|---|---|---|---|---|---|---|---|---|---|---|---|---|---|---|---|
| | | | 35 | | | | | 40 | | | | | 45 | | |

| Lys | Ile | Ile | Asp | Leu | Glu | Glu | Ala | Glu | Asp | Glu | Ile | Glu | Asp | Ile | Gln |
|---|---|---|---|---|---|---|---|---|---|---|---|---|---|---|---|
| | | 50 | | | | | 55 | | | | | 60 | | | |

```
Gln Glu Ile Thr Val Leu Ser Gln Cys Asp Ser Pro Tyr Ile Thr Arg
 65              70                  75                  80

Tyr Phe Gly Ser Tyr Leu Lys Ser Thr Lys Leu Trp Ile Ile Met Glu
                 85                  90                  95

Tyr Leu Gly Gly Gly Ser Ala Leu Asp Leu Leu Lys Pro Gly Pro Leu
            100             105             110

Glu Glu Thr Tyr Ile Ala Thr Ile Leu Arg Glu Ile Leu Lys Gly Leu
        115             120             125

Asp Tyr Leu His Ser Glu Arg Lys Ile His Arg Asp Ile Lys Ala Ala
    130             135             140

Asn Val Leu Leu Ser Glu Gln Gly Asp Val Leu Ala Gly Gly Leu Trp
145             150             155                         160

Gly Ser Arg Gln Leu Thr Asp Thr Gln Ile Lys Arg Asn Thr Phe Val
                165             170                 175

Gly Thr Pro Phe Trp Met Ala Pro Glu Val Ile Lys Gln Ser Ala Tyr
            180             185             190

Asp Phe Lys Ala Asp Ile Trp Ser Leu Gly Ile Thr Ala Ile Glu Leu
        195             200             205

Ala Lys Gly Glu Pro Pro Asn Ser Asp Leu His Pro Met Arg Val Leu
    210             215             220

Phe Leu Ile Pro Lys Asn Ser Pro Pro Thr Leu Glu Gly Gln His Ser
225             230             235                         240

Lys Pro Phe Lys Glu Phe Val Glu Ala Cys Leu Asn Lys Asp Pro Arg
            245             250             255

Phe Arg Pro Thr Ala Lys Glu Leu Leu Lys His Lys Phe Ile Thr Arg
        260             265             270

Tyr Thr Lys Lys Thr Ser Phe Leu Thr Glu Leu Ile Asp Arg Tyr Lys
        275             280             285

Arg Trp Lys Ser Glu Gly His Gly Glu Glu Ser Ser Ser Glu Asp Ser
    290             295             300

Asp Ile Asp Gly Glu Ala Glu Asp Gly Glu Gln Gly Pro Ile Trp Thr
305             310             315                         320

Phe Pro Pro Thr Ile Arg Pro Ser Pro His Ser Lys Leu His Lys Gly
            325             330             335

Thr Ala Leu His Ser Ser Gln Lys Pro Ala Glu Pro Val Lys Arg Gln
        340             345             350

Pro Arg Ser Gln Cys Leu Ser Thr Leu Val Arg Pro Val Phe Gly Glu
        355             360             365

Leu Lys Arg Ser Thr Ser Arg Ala Ala Gly Ala Trp Val Arg Trp Arg
    370             375             380

Ser Trp Arg Thr Pro Ser Ala Trp Pro Arg Ser Pro Ala Pro Ala Ser
385             390             395                         400

Gln Thr Ser
```

( 2 ) INFORMATION FOR SEQ ID NO:4:

( i ) SEQUENCE CHARACTERISTICS:
        ( A ) LENGTH: 2161 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
        ( A ) LIBRARY:
        ( B ) CLONE: Consensus (xi) SEQUENCE DESCRIPTION: SEQ ID NO:4:

```
CGTTAGGCCC GGGCGTGGCG GGGCCCCGGC GGCCTGGGGG GTCTCCTGGG CCCCCCCCA     60
CCCATGGAGC CCGCCGCCCC GGAGGTCGGT CTCAGATGAC TGAACTGGGC ACCGAGCGCC    120
CCTGGTGTCC CTCGCAGTGG ACTGACGCCG CAGGGGCGAG CTAGCCGGCT CCGCGCCTCT    180
CCGCGGGATC CAGACGNCTC CTGGGGCTGC TGGCGGAGGG TCTGACGCGG CGCGGCCATG    240
GCTCACCTCC GGGGATTTGC CAACCAGCAC TCTCGAGTGG ACCCTGAGGA GCTCTTCACC    300
AAGCTCGACC GCATTGGCAA GGGCTCGTTT GGGGAGGTCT ACAAGGGCAT CGATAACCAC    360
ACAAAGGAGG TGGTGGCCAT CAAGATCATC GACCTGGAGG AGGCCGAGGA TGAGATCGAG    420
GACATCCAGC AGGAGATCAC TGTCCTCAGT CAGTGCGACA GCCCCTACAT CACCCGCTAC    480
TTTGGCTCCT ACCTAAAGAG CACCAAGCTA TGGATCATCA TGGAGTACCT GGGCGGCGGC    540
TCAGCACTGG ACTTGCTTAA ACCAGGTCCC CTGGAGGAGA CATACATTGC CACGATCCTG    600
CGGGAGATTC TGAAGGGCCT GGATTATCTG CACTCCGAAC GCAAGATCCA CCGAGACATC    660
AAAGCTGCCA ACGTGCTACT CTCGGAGCAG GGTGACGTGT TAGCTGGCGG ACTTTGGGGT    720
AGCAGGCAGC TCACAGACAC GCAGATTAAG AGGAACACAT TCGTGGGCAC CCCCTTCTGG    780
ATGGCACCTG AGGTCATCAA GCAGTCGGCC TACGACTTCA AGGCTGACAT CTGGTCCCTG    840
GGGATCACAG CCATCGAGCT CGCCAAGGGG GAGCCTCCAA ACTCTGACCT CCACCCCATG    900
CGCGTCCTGT TCCTGATTCC CAAGAACAGC CCACCCACAC TGGAGGGCCA GCACAGCAAG    960
CCCTTCAAGG AGTTCGTGGA GGCCTGCCTC AACAAAGACC CCCGATTCCG GCCCACGGCC   1020
AAGGAGCTCC TGAAGCACAA GTTCATCACA CGCTACACCA AGAAGACCTC CTTCCTCACG   1080
GAGCTCATCG ACCGCTATAA GCGCTGGAAG TCAGAGGGGC ATGGCGAGGA GTCCAGCTCT   1140
GAGGACTCTG ACATTGATGG CGAGGCGGAG GACGGGGAGC AGGGCCCCAT CTGGACGTTC   1200
CCCCCTACCA TCCGGCCGAG TCCACACAGC AAGCTTCACA AGGGGACGGC CCTGCACAGT   1260
TCACAGAAGC CTGCGGAGCC CGTCAAGAGG CAGCCGAGGT CCCAGTGCCT GTCCACGCTG   1320
GTCCGGCCCG TTTTCGGAGA GCTCAAGAGA AGCACAAGCA GAGCGGCGGG AGCGTGGGTG   1380
CGCTGGAGGA GCTGGAGAAC GCCTTCAGCC TGGCCGAGGA GTCCTGCCCC GGCATCTCAG   1440
ACAAGCTGAT GGTGCACCTG GTGGAGCGAG TGCAGAGGTT TTCACACAAC AGAAACCACC   1500
TGACATCCAC CCGCTGAAGC GCACTGCTGT TCAGATAGGG GACGGAAGGT CGTTTGTTTT   1560
TGTTCTGAGC TCCATAAGAA CTGTGCTGAC TTGGAAGGTG CCCTGTGCTA TGTCGTGCCT   1620
GCAGGGACAC GTCGGATCCC GTGGGCCTCA CATGCCAGGT CACCAGGTCA CCGTCTCCTT   1680
CCACCCCTGC AGTGTGCTGT TGTGCACGTC AGGGACGCTG TTCTCTATGC CCACTGCCCT   1740
CCTCCCTCTC CTGGCCCAGC AGTATTGCTC ACGGGGCTC CAGCCGCCGG CGTGGCCCTC    1800
ATGAGCTACG CCTGGGTCTT CTGCAGACTC ATGCAGCCCT ATGGCCGCTC AGACCAAGGC   1860
GCAGAGCAAC TATCAGGGCA GCTCTGCCTC CTCCTCCCAT GAGGTGGGGA GAGGCAACAG   1920
GGCAGCCCCC AGAGGAGTGT CCTGGCCGCT GTCCTCCCGG GGCCCATGAT GGCCATAGAT   1980
TTGCCTTGTG GTGTTGGATC AGGTACTGTG TCTGCTCATA AGTACTTGTG TCATCCAGAA   2040
TGTTTTGTTT TTAAGAAAA TTGAATTACT TGTTTCCTGA AATATTCTGA GGTTAATATG    2100
TTAGTTTTCA TAGAACATTG AGAGGCCCCT GCCACTTTCA ATAAAGACCT GACTTGGAGN   2160
C                                                                  2161
```

(2) INFORMATION FOR SEQ ID NO:5:

( i ) SEQUENCE CHARACTERISTICS:
    ( A ) LENGTH: 431 amino acids
    ( B ) TYPE: amino acid
    ( C ) STRANDEDNESS: single
    ( D ) TOPOLOGY: linear ( i i ) MOLECULE TYPE: peptide ( v i i ) IMMEDIATE SOURCE:
    ( A ) LIBRARY:
    ( B ) CLONE: Consensus ( x i ) SEQUENCE DESCRIPTION: SEQ ID NO:5:

```
Met Ala Val Lys Thr Glu Ala Ala Lys Gly Thr Leu Thr Tyr Ser Arg
 1               5                  10                  15

Met Arg Gly Met Val Ala Ile Leu Ile Ala Phe Met Lys Gln Arg Arg
            20                  25                  30

Met Gly Leu Asn Asp Phe Ile Gln Lys Ile Ala Asn Asn Ser Tyr Ala
            35                  40                  45

Cys Lys His Pro Glu Val Gln Ser Ile Leu Lys Ile Ser Gln Pro Gln
 50                      55                  60

Glu Pro Glu Leu Met Asn Ala Asn Pro Ser Pro Pro Ser Pro Ser
 65                  70                      75                  80

Gln Gln Ile Asn Leu Gly Pro Ser Ser Asn Pro His Ala Lys Pro Ser
                85                  90                      95

Asp Phe His Phe Leu Lys Val Ile Gly Lys Gly Ser Phe Gly Lys Val
                100                 105                 110

Leu Leu Ala Arg His Lys Ala Glu Glu Val Phe Tyr Ala Val Lys Val
            115                 120                 125

Leu Gln Lys Lys Ala Ile Leu Lys Lys Lys Glu Glu Lys His Ile Met
    130                 135                 140

Ser Glu Arg Asn Val Leu Leu Lys Asn Val Lys His Pro Phe Leu Val
145                     150                 155                 160

Gly Leu His Phe Ser Phe Gln Thr Ala Asp Lys Leu Tyr Phe Val Leu
                165                 170                 175

Asp Tyr Ile Asn Gly Gly Glu Leu Phe Tyr His Leu Gln Arg Glu Arg
            180                 185                 190

Cys Phe Leu Glu Pro Arg Ala Arg Ser Tyr Ala Ala Glu Ile Ala Ser
        195                 200                 205

Ala Leu Gly Tyr Leu His Ser Leu Asn Ile Val Tyr Arg Asp Leu Lys
    210                 215                 220

Pro Glu Asn Ile Leu Leu Asp Ser Gln Gly His Ile Val Leu Thr Asp
225                 230                 235                 240

Phe Gly Leu Cys Lys Glu Asn Ile Glu His Asn Ser Thr Thr Ser Thr
                245                 250                 255

Phe Cys Gly Thr Pro Glu Tyr Leu Ala Pro Glu Val Leu His Lys Gln
            260                 265                 270

Pro Tyr Asp Arg Thr Val Asp Trp Trp Cys Leu Gly Ala Val Leu Tyr
        275                 280                 285

Glu Met Leu Tyr Gly Leu Pro Pro Phe Tyr Ser Arg Asn Thr Ala Glu
    290                 295                 300

Met Tyr Asp Asn Ile Leu Asn Lys Pro Leu Gln Leu Lys Pro Asn Ile
305                 310                 315                 320

Thr Asn Ser Ala Arg His Leu Leu Glu Gly Leu Leu Gln Lys Asp Arg
                325                 330                 335

Thr Lys Arg Leu Gly Ala Lys Asp Asp Phe Met Glu Ile Lys Ser His
            340                 345                 350
```

| | | | | | | | | | | | | | | | |
|---|---|---|---|---|---|---|---|---|---|---|---|---|---|---|---|
| Val | Phe | Phe<br>355 | Ser | Leu | Ile | Asn | Trp<br>360 | Asp | Asp | Leu | Ile | Asn<br>365 | Lys | Lys | Ile |
| Thr | Pro<br>370 | Pro | Phe | Asn | Pro<br>375 | Asn | Val | Ser | Gly | Pro<br>380 | Asn | Asp | Leu | Arg | His |
| Phe<br>385 | Asp | Pro | Glu | Phe<br>390 | Thr | Glu | Glu | Pro | Val<br>395 | Pro | Asn | Ser | Ile | Gly<br>400 | Lys |
| Ser | Pro | Asp | Ser<br>405 | Val | Leu | Val | Thr | Ala<br>410 | Ser | Val | Lys | Glu | Ala<br>415 | Ala | Glu |
| Ala | Phe | Leu | Gly<br>420 | Phe | Ser | Tyr | Ala | Pro<br>425 | Pro | Thr | Asp | Ser | Phe<br>430 | Leu | |

(2) INFORMATION FOR SEQ ID NO:6:

(i) SEQUENCE CHARACTERISTICS:
        (A) LENGTH: 2311 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (A) LIBRARY:
        (B) CLONE: Consensus (xi) SEQUENCE DESCRIPTION: SEQ ID NO:6:

```
GCGGTGGTGA TGGCGGTGAA AACTGAGGCT GCTAAGGGCA CCCTCACTTA CTCCAGGATG      60
AGGGGCATGG TGGCAATTCT CATCGCTTTC ATGAAGCAGA GGAGGATGGG TCTGAACGAC     120
TTTATTCAGA AGATTGCCAA TAACTCCTAT GCATGCAAAC ACCCTGAAGT TCAGTCCATC     180
TTGAAGATCT CCCAACCTCA GGAGCCTGAG CTTATGAATG CCAACCCTTC TCCTCCACCA     240
AGTCCTTCTC AGCAAATCAA CCTTGGCCCG TCGTCCAATC CTCATGCTAA ACCATCTGAC     300
TTTCACTTCT TGAAAGTGAT CGGAAAGGGC AGTTTTGGAA AGGTTCTTCT AGCAAGACAC     360
AAGGCAGAAG AAGTGTTCTA TGCAGTCAAA GTTTTACAGA AGAAAGCAAT CCTGAAAAAG     420
AAAGAGGAGA AGCATATTAT GTCGGAGCGG AATGTTCTGT TGAAGAATGT GAAGCACCCT     480
TTCCTGGTGG GCCTTCACTT CTCTTTCCAG ACTGCTGACA AATTGTACTT TGTCCTAGAC     540
TACATTAATG GTGGAGAGTT GTTCTACCAT CTCCAGAGGG AACGCTGCTT CCTGGAACCA     600
CGGGCTCGTT CCTATGCTGC TGAAATAGCC AGTGCCTTGG GCTACCTGCA TTCACTGAAC     660
ATCGTTTATA GAGACTTAAA ACCAGAGAAT ATTTTGCTAG ATTCACAGGG ACACATTGTC     720
CTTACTGACT TCGGACTCTG CAAGGAGAAC ATTGAACACA ACAGCACAAC ATCCACCTTC     780
TGTGGCACGC CGGAGTATCT CGCACCTGAG GTGCTTCATA AGCAGCCTTA TGACAGGACT     840
GTGGACTGGT GGTGCCTGGG AGCTGTCTTG TATGAGATGC TGTATGGCCT GCCGCCTTTT     900
TATAGCCGAA ACACAGCTGA AATGTACGAC AACATTCTGA ACAAGCCTCT CCAGCTGAAA     960
CCAAATATTA CAAATTCCGC AAGACACCTC CTGGAGGGCC TCCTGCAGAA GGACAGGACA    1020
AAGCGGCTCG GGCCAAGGA TGACTTCATG GAGATTAAGA GTCATGTCTT CTTCTCCTTA    1080
ATTAACTGGG ATGATCTCAT TAATAAGAAG ATTACTCCCC CTTTTAACCC AAATGTGAGT    1140
GGGCCCAACG ACCTACGGCA CTTTGACCCC GAGTTTACCG AAGAGCCTGT CCCCAACTCC    1200
ATTGGCAAGT CCCCTGACAG CGTCCTCGTC ACAGCCAGCG TCAAGGAAGC TGCCGAGGCT    1260
TTCCTAGGCT TTTCCTATGC GCCTCCCACG GACTCTTTCC TCTGAACCCT GTTAGGGCTT    1320
GGTTTTAAAG GATTTTATGT GTGTTTCCGA ATGTTTTAGT TAGCCTTTTG GTGGAGCCGC    1380
CAGCTGACAG GACATCTTAC AAGAGAATTT GCACATCTCT GGAAGCTTAG CAATCTTATT    1440
```

```
GCACACTGTT CGCTGGAAGC TTTTTGAAGA GCACATTCTC CTCAGTGAGC TCATGAGGTT    1500

TTCATTTTTA TTCTTCCTTC CAACGTGGTG CTATCTCTGA AACGAGCGTT AGAGTGCCGC    1560

CTTAGACGGA GGCAGGAGTT TCGTTAGAAA GCGGACGCTG TTCTAAAAAA GGTCTCCTGC    1620

AGATCTGTCT GGGCTGTGAT GACGAATATT ATGAAATGTG CCTTTTCTGA AGAAATTGT    1680

GTTAGCTCCA AAGCTTTTCC TATCGCAGTG TTTCAGTTCT TTATTTTCCC TTGTGGATAT    1740

GCTGTGTGAA CCGTCGTGTG AGTGTGGTAT GCCTGATCAC AGATGGATTT TGTTATAAGC    1800

ATCAATGTGA CACTTGCAGG ACACTACAAC GTGGGACATT GTTTGTTTCT TCCATATTTG    1860

GAAGATAAAT TTATGTGTAG ACTTTTTTGT AAGATACGGT TAATAACTAA AATTTATTGA    1920

AATGGTCTTG CAATGACTCG TATTCAGATG CTTAAAGAAA GCATTGCTGC TACAAATATT    1980

TCTATTTTTA GAAAGGGTTT TTATGGACCA ATGCCCCAGT TGTCAGTCAG AGCCGTTGGT    2040

GTTTTTCATT GTTTAAAATG TCACCTGTAA AATGGGCATT ATTTATGTTT TTTTTTTTGC    2100

ATTCCTGATA ATTGTATGTA TTGTATAAAG AACGTCTGTA CATTGGGTTA TAACACTAGT    2160

ATATTTAAAC TTACAGGCTT ATTTGTAATG TAAACCACCA TTTTAATGTA CTGTAATTAA    2220

CATGGTTATA ATACGNACAA TCCTTCCCTC ATCCCATCAC ACAACTTTTT TTGTGTGTGA    2280

TAAACTGATT TTGGTTTGCA ATAAAACCTT G                                   2311
```

(2) INFORMATION FOR SEQ ID NO:7:

(i) SEQUENCE CHARACTERISTICS:
        (A) LENGTH: 239 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (A) LIBRARY: GenBank
        (B) CLONE: 1082115

(xi) SEQUENCE DESCRIPTION: SEQ ID NO:7:

```
Val Phe Glu Met Val Asp Gln Lys Ala Arg Gln Asp Cys Leu Lys Glu
 1               5                  10                  15

Ile Asp Leu Leu Lys Gln Leu Asn His Val Asn Val Ile Arg Tyr Tyr
                20                  25                  30

Ala Ser Phe Ile Asp Asn Asn Gln Leu Asn Ile Val Leu Glu Leu Ala
            35                  40                  45

Glu Ala Gly Asp Met Ser Arg Met Ile Lys His Phe Lys Lys Gly Gly
        50                  55                  60

Arg Leu Ile Pro Glu Lys Thr Ile Trp Lys Tyr Phe Val Gln Leu Ala
 65                  70                  75                  80

Arg Ala Leu Ala His Met His Ser Lys Arg Ile Met His Arg Asp Ile
                85                  90                  95

Lys Pro Ala Asn Val Phe Ile Thr Gly Asn Gly Ile Val Lys Leu Gly
                100                 105                 110

Asp Leu Gly Leu Gly Arg Phe Phe Ser Ser Lys Thr Ala Ala His
            115                 120                 125

Ser Leu Val Gly Thr Pro Tyr Tyr Met Ser Pro Glu Arg Ile Gln Glu
        130                 135                 140

Ser Gly Tyr Asn Phe Lys Ser Asp Leu Trp Ser Thr Gly Cys Leu Leu
145                 150                 155                 160

Tyr Glu Met Ala Ala Leu Gln Ser Pro Phe Tyr Gly Asp Lys Met Asn
                165                 170                 175
```

-continued

| Leu | Tyr | Ser | Leu | Cys | Lys | Lys | Ile | Glu | Asn | Cys | Glu | Tyr | Pro | Pro | Leu |
|---|---|---|---|---|---|---|---|---|---|---|---|---|---|---|---|
| | | | 180 | | | | 185 | | | | | | 190 | | |

| Pro | Ala | Asp | Ile | Tyr | Ser | Thr | Gln | Val | Ser | Ala | Asn | Leu | Cys | Phe | Val |
|---|---|---|---|---|---|---|---|---|---|---|---|---|---|---|---|
| | | 195 | | | | | 200 | | | | | 205 | | | |

| Gln | Leu | Ser | Ser | Ala | Thr | Trp | Tyr | Pro | Val | Val | Tyr | Phe | Gln | Lys | Leu |
|---|---|---|---|---|---|---|---|---|---|---|---|---|---|---|---|
| 210 | | | | | | 215 | | | | | 220 | | | | |

| Gln | Asn | Asp | Gln | Arg | Pro | Val | Lys | Phe | Tyr | Arg | Phe | Val | Pro | Arg | |
|---|---|---|---|---|---|---|---|---|---|---|---|---|---|---|---|
| 225 | | | | | 230 | | | | | 235 | | | | | |

(2) INFORMATION FOR SEQ ID NO:8:

(i) SEQUENCE CHARACTERISTICS:
        (A) LENGTH: 487 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (A) LIBRARY: GenBank
        (B) CLONE: 1117791

(xi) SEQUENCE DESCRIPTION: SEQ ID NO:8:

| Met | Glu | Thr | Val | Gln | Leu | Arg | Asn | Pro | Pro | Arg | Arg | Gln | Leu | Lys | Lys |
|---|---|---|---|---|---|---|---|---|---|---|---|---|---|---|---|
| 1 | | | | 5 | | | | | 10 | | | | | 15 | |

| Leu | Asp | Glu | Asp | Ser | Leu | Thr | Lys | Gln | Pro | Glu | Glu | Val | Phe | Asp | Val |
|---|---|---|---|---|---|---|---|---|---|---|---|---|---|---|---|
| | | | 20 | | | | | 25 | | | | | 30 | | |

| Leu | Glu | Lys | Leu | Gly | Glu | Gly | Ser | Tyr | Gly | Ser | Val | Tyr | Lys | Ala | Ile |
|---|---|---|---|---|---|---|---|---|---|---|---|---|---|---|---|
| | | 35 | | | | | 40 | | | | | 45 | | | |

| His | Lys | Glu | Thr | Gly | Gln | Ile | Val | Ala | Ile | Lys | Gln | Val | Pro | Val | Glu |
|---|---|---|---|---|---|---|---|---|---|---|---|---|---|---|---|
| | 50 | | | | | 55 | | | | | 60 | | | | |

| Ser | Asp | Leu | Gln | Glu | Ile | Ile | Lys | Glu | Ile | Ser | Ile | Met | Gln | Gln | Cys |
|---|---|---|---|---|---|---|---|---|---|---|---|---|---|---|---|
| 65 | | | | | 70 | | | | | 75 | | | | | 80 |

| Asp | Ser | Pro | His | Val | Val | Lys | Tyr | Tyr | Gly | Ser | Tyr | Phe | Lys | Asn | Thr |
|---|---|---|---|---|---|---|---|---|---|---|---|---|---|---|---|
| | | | | 85 | | | | | 90 | | | | | 95 | |

| Asp | Leu | Trp | Ile | Val | Met | Glu | Tyr | Cys | Gly | Ala | Gly | Ser | Val | Ser | Asp |
|---|---|---|---|---|---|---|---|---|---|---|---|---|---|---|---|
| | | | 100 | | | | | 105 | | | | | 110 | | |

| Ile | Ile | Arg | Leu | Arg | Asn | Lys | Thr | Leu | Thr | Glu | Asp | Glu | Ile | Ala | Thr |
|---|---|---|---|---|---|---|---|---|---|---|---|---|---|---|---|
| | | 115 | | | | | 120 | | | | | 125 | | | |

| Ile | Leu | Gln | Ser | Thr | Leu | Lys | Gly | Leu | Glu | Tyr | Leu | His | Phe | Met | Arg |
|---|---|---|---|---|---|---|---|---|---|---|---|---|---|---|---|
| | 130 | | | | | 135 | | | | | 140 | | | | |

| Lys | Ile | His | Arg | Asp | Ile | Lys | Ala | Gly | Asn | Ile | Leu | Leu | Asn | Thr | Glu |
|---|---|---|---|---|---|---|---|---|---|---|---|---|---|---|---|
| 145 | | | | | 150 | | | | | 155 | | | | | 160 |

| Gly | His | Ala | Lys | Leu | Ala | Asp | Phe | Gly | Val | Ala | Gly | Gln | Leu | Thr | Asp |
|---|---|---|---|---|---|---|---|---|---|---|---|---|---|---|---|
| | | | | 165 | | | | | 170 | | | | | 175 | |

| Thr | Met | Ala | Lys | Arg | Asn | Thr | Val | Ile | Gly | Thr | Pro | Phe | Trp | Met | Ala |
|---|---|---|---|---|---|---|---|---|---|---|---|---|---|---|---|
| | | | 180 | | | | | 185 | | | | | 190 | | |

| Pro | Glu | Val | Ile | Gln | Glu | Ile | Gly | Tyr | Asn | Cys | Val | Ala | Asp | Ile | Trp |
|---|---|---|---|---|---|---|---|---|---|---|---|---|---|---|---|
| | | 195 | | | | | 200 | | | | | 205 | | | |

| Ser | Leu | Gly | Ile | Thr | Ala | Ile | Glu | Met | Ala | Glu | Gly | Lys | Arg | Pro | Tyr |
|---|---|---|---|---|---|---|---|---|---|---|---|---|---|---|---|
| | 210 | | | | | 215 | | | | | 220 | | | | |

| Ala | Asp | Ile | His | Pro | Met | Arg | Ala | Ile | Phe | Met | Ile | Pro | Thr | Asn | Pro |
|---|---|---|---|---|---|---|---|---|---|---|---|---|---|---|---|
| 225 | | | | | 230 | | | | | 235 | | | | | 240 |

| Pro | Pro | Thr | Phe | Arg | Lys | Pro | Glu | Leu | Trp | Ser | Asp | Asn | Phe | Thr | Asp |
|---|---|---|---|---|---|---|---|---|---|---|---|---|---|---|---|
| | | | | 245 | | | | | 250 | | | | | 255 | |

| Phe | Val | Lys | Gln | Cys | Leu | Val | Lys | Ser | Pro | Glu | Gln | Arg | Ala | Thr | Ala |
|---|---|---|---|---|---|---|---|---|---|---|---|---|---|---|---|
| | | | 260 | | | | | 265 | | | | | 270 | | |

-continued

```
Thr Gln Leu Leu Gln His Pro Phe Val Arg Ser Ala Lys Gly Val Ser
    275                 280                 285
Ile Leu Arg Asp Leu Ile Asn Glu Ala Met Asp Val Lys Leu Lys Arg
    290                 295                 300
Gln Glu Ser Gln Gln Arg Glu Met Asp Gln Asp Glu Glu Asn Ser
305                 310                 315                 320
Glu Glu Asp Glu Met Asp Ser Gly Thr Met Val Arg Ala Val Gly Asp
                325                 330                 335
Glu Met Gly Thr Val Arg Val Ala Ser Thr Met Thr Asp Gly Ala Asn
            340                 345                 350
Thr Met Ile Glu His Asp Asp Thr Leu Pro Ser Gln Leu Gly Thr Met
        355                 360                 365
Val Ile Asn Ala Glu Asp Glu Glu Glu Gly Thr Met Lys Arg Arg
    370                 375                 380
Asp Glu Thr Met Gln Pro Ala Lys Pro Ser Phe Leu Glu Tyr Phe Glu
385                 390                 395                 400
Gln Lys Glu Lys Glu Asn Gln Ile Asn Ser Phe Gly Lys Ser Val Pro
                405                 410                 415
Gly Pro Leu Lys Asn Ser Ser Asp Trp Lys Ile Pro Gln Asp Gly Asp
            420                 425                 430
Tyr Glu Phe Leu Lys Ser Trp Thr Val Glu Asp Leu Gln Lys Arg Leu
        435                 440                 445
Leu Ala Leu Asp Pro Met Met Glu Gln Glu Ile Glu Glu Ile Arg Gln
    450                 455                 460
Lys Tyr Gln Ser Lys Arg Gln Pro Ile Leu Asp Ala Ile Glu Ala Lys
465                 470                 475                 480
Lys Arg Arg Gln Gln Asn Phe
                485
```

(2) INFORMATION FOR SEQ ID NO:9:

(i) SEQUENCE CHARACTERISTICS:
        (A) LENGTH: 430 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (A) LIBRARY: GenBank
        (B) CLONE: 294637

(xi) SEQUENCE DESCRIPTION: SEQ ID NO:9:

```
Met Thr Val Lys Thr Glu Ala Ala Arg Ser Thr Leu Thr Tyr Ser Arg
1               5                   10                  15
Met Arg Gly Met Val Ala Ile Leu Ile Ala Phe Met Lys Gln Arg Arg
            20                  25                  30
Met Gly Leu Asn Asp Phe Ile Gln Lys Leu Ala Asn Asn Ser Tyr Ala
        35                  40                  45
Cys Lys His Pro Glu Val Gln Ser Tyr Leu Lys Ile Ser Gln Pro Gln
    50                  55                  60
Glu Pro Glu Leu Met Asn Ala Asn Pro Ser Pro Pro Ser Pro Ser
65                  70                  75                  80
Gln Gln Ile Asn Leu Gly Pro Ser Ser Asn Pro His Ala Lys Pro Ser
                85                  90                  95
Asp Phe His Phe Leu Lys Val Ile Gly Lys Gly Ser Phe Gly Lys Val
            100                 105                 110
```

-continued

| | | | | | | | | | | | | | | |
|---|---|---|---|---|---|---|---|---|---|---|---|---|---|---|
| Leu | Leu | Ala 115 | Arg | His | Lys | Ala | Glu 120 | Glu | Ala | Phe | Tyr | Ala 125 | Lys | Val |
| Leu | Gln 130 | Lys | Lys | Ala | Ile | Leu 135 | Lys | Lys | Lys | Glu | Glu 140 | Lys | His | Ile | Met |
| Ser 145 | Glu | Arg | Asn | Val | Leu 150 | Leu | Lys | Asn | Val | Lys 155 | His | Pro | Phe | Leu | Val 160 |
| Gly | Leu | His | Phe | Ser 165 | Phe | Gln | Thr | Ala | Asp 170 | Lys | Leu | Tyr | Phe | Val 175 | Leu |
| Asp | Tyr | Ile | Asn 180 | Gly | Gly | Glu | Leu | Phe 185 | Tyr | His | Leu | Gln | Arg 190 | Glu | Arg |
| Cys | Phe | Leu 195 | Glu | Pro | Arg | Ala | Arg 200 | Phe | Tyr | Ala | Ala | Glu 205 | Ile | Ala | Ser |
| Ala | Leu 210 | Gly | Tyr | Leu | His | Ser 215 | Leu | Asn | Ile | Val | Tyr 220 | Arg | Asp | Leu | Lys |
| Pro 225 | Glu | Asn | Ile | Leu | Leu 230 | Asp | Ser | Gln | Gly | His 235 | Ile | Val | Leu | Thr | Asp 240 |
| Phe | Gly | Leu | Cys | Lys 245 | Glu | Asn | Ile | Glu | His 250 | Asn | Gly | Thr | Thr | Ser 255 | Thr |
| Phe | Cys | Gly | Thr 260 | Pro | Glu | Tyr | Leu | Ala 265 | Pro | Glu | Val | Leu | His 270 | Lys | Gln |
| Pro | Tyr | Asp 275 | Arg | Thr | Val | Asp | Trp 280 | Trp | Cys | Leu | Gly | Ala 285 | Val | Leu | Tyr |
| Glu | Met 290 | Leu | Tyr | Gly | Leu | Pro 295 | Pro | Phe | Tyr | Ser | Arg 300 | Asn | Thr | Ala | Glu |
| Met 305 | Tyr | Asp | Asn | Ile | Leu 310 | Asn | Lys | Pro | Leu | Gln 315 | Leu | Lys | Asn | Ile | Thr 320 |
| Asn | Ser | Ala | Arg | His 325 | Leu | Leu | Glu | Gly | Leu 330 | Leu | Gln | Lys | Asp | Arg 335 | Thr |
| Lys | Arg | Leu | Gly 340 | Ala | Lys | Asp | Asp | Phe 345 | Met | Glu | Ile | Lys | Ser 350 | His | Ile |
| Phe | Phe | Ser 355 | Leu | Ile | Asn | Trp | Asp 360 | Asp | Leu | Ile | Asn | Lys 365 | Lys | Ile | Thr |
| Pro | Pro 370 | Phe | Asn | Pro | Asn | Val 375 | Ser | Gly | Pro | Ser | Asp 380 | Leu | Arg | His | Phe |
| Asp 385 | Pro | Glu | Phe | Thr | Glu 390 | Glu | Pro | Val | Pro | Ser 395 | Ser | Ile | Gly | Arg | Ser 400 |
| Pro | Asp | Ser | Ile | Leu 405 | Val | Thr | Ala | Ser | Val 410 | Lys | Glu | Ala | Ala | Glu 415 | Ala |
| Phe | Leu | Gly | Phe 420 | Ser | Tyr | Ala | Pro | Pro 425 | Met | Asp | Ser | Phe | Leu 430 | | |

What is claimed is:

1. An isolated and purified polynucleotide sequence encoding the polypeptide comprising the amino acid sequence of SEQ ID NO:1.

2. The isolated and purified polynucleotide sequence of claim 1 comprising the sequence of SEQ ID NO:2.

3. An isolated and purified polynucleotide sequence which is complementary to the polynucleotide sequence of claim 2.

4. An expression vector comprising the polynucleotide sequence of claim 1.

5. A host cell comprising the expression vector of claim 4.

6. A method for producing a polypeptide comprising the amino acid sequence shown in SEQ ID NO:1, the method comprising the steps of:

a) culturing the host cell of claim 5 under conditions suitable for the expression of the polypeptide; and b) recovering the polypeptide from the host cell culture.

7. An isolated and purified polynucleotide sequence encoding the polypeptide comprising the amino acid sequence of SEQ ID NO:3.

8. The isolated and purified polynucleotide sequence of claim 7 comprising the sequence of SEQ ID NO:4.

9. An isolated and purified polynucleotide sequence which is complementary to the polynucleotide sequence of claim 8.

10. An expression vector comprising the polynucleotide sequence of claim 7.

11. A host cell comprising the expression vector of claim 10.

12. A method for producing a polypeptide comprising the amino acid sequence shown in SEQ ID NO:3, the method comprising the steps of:

a) culturing the host cell of claim 11 under conditions suitable for the expression of the polypeptide; and
b) recovering the polypeptide from the host cell culture.

* * * * *